(12) United States Patent
Lavallee et al.

(10) Patent No.: US 12,390,235 B2
(45) Date of Patent: Aug. 19, 2025

(54) SURGICAL SYSTEM FOR CUTTING AN ANATOMICAL STRUCTURE ACCORDING TO AT LEAST ONE TARGET PLANE

(71) Applicant: Orthotaxy S.A.S., Gières (FR)

(72) Inventors: Stéphane Lavallee, Saint Martin d'Uriage (FR); Nicolas Demanget, Saint-Egrève (FR); Hervé Collet, Chatenay (FR); Daniel Girardeau-Montaut, Gieres (FR); Laurence Chabanas, Crets en Belledonne (FR); François Urvoy, Sainte Nazaire les Eymes (FR)

(73) Assignee: Orthotaxy S.A.S., Gières (FR)

( * ) Notice: Subject to any disclaimer, the term of this patent is extended or adjusted under 35 U.S.C. 154(b) by 0 days.

(21) Appl. No.: 18/600,233

(22) Filed: Mar. 8, 2024

(65) Prior Publication Data

US 2024/0293130 A1    Sep. 5, 2024

Related U.S. Application Data

(63) Continuation of application No. 16/467,816, filed as application No. PCT/EP2017/077370 on Oct. 25, 2017, now Pat. No. 11,974,761.

(30) Foreign Application Priority Data

Dec. 8, 2016  (EP) ..................... 16306645

(51) Int. Cl.
*A61B 17/17*   (2006.01)
*A61B 17/14*   (2006.01)
(Continued)

(52) U.S. Cl.
CPC ........ *A61B 17/1764* (2013.01); *A61B 17/142* (2016.11); *A61B 17/1675* (2013.01);
(Continued)

(58) Field of Classification Search
CPC ........ A61B 17/1675; A61B 17/14–149; A61B 17/15–158; A61B 34/20; A61B 34/30;
(Continued)

(56) References Cited

U.S. PATENT DOCUMENTS 5,236,432 A * 8/1993 Matsen, III ............ A61B 17/15
                                                                    700/246
5,403,319 A    4/1995 Matsen, III et al.
(Continued)

FOREIGN PATENT DOCUMENTS

CN            1243690 A      2/2000
CN          101484086 A      7/2009
(Continued)

OTHER PUBLICATIONS

Kerschbaumer, et al., "A Mechatronic System for the Implantation of the Acetabular Component in Total Hip Alloarthroplasy", University of Siegen, Hoelderlinstr, 2001, 2 pages.
(Continued)

*Primary Examiner* — Matthew J Lawson
(74) *Attorney, Agent, or Firm* — Condo Roccia Koptiw LLP

(57) ABSTRACT

Described are surgical systems comprising a robotic device comprising a cutting tool, an actuation unit having at least two motorized rotational degrees of freedom about respective rotational axes that are substantially orthogonal to each other, and configured for adjusting a position and orientation of the cutting tool relative to each target plane, a planar mechanism connecting the last segment of the actuation unit to the cutting tool, a passive articulated lockable holding arm supporting the actuation unit, a tracking unit configured to determine in real time the pose of the cutting plane with respect to the coordinate system of the anatomical structure, a control unit configured to determine the pose of the cutting (Continued)

plane with respect to the target plane and to control the actuation unit to bring the cutting plane into alignment with the target plane.

20 Claims, 32 Drawing Sheets

(51) Int. Cl.
  *A61B 17/15* (2006.01)
  *A61B 17/16* (2006.01)
  *A61B 17/3203* (2006.01)
  *A61B 17/3211* (2006.01)
  *A61B 34/30* (2016.01)
  *A61B 18/00* (2006.01)
  *A61B 18/20* (2006.01)

(52) U.S. Cl.
  CPC ...... *A61B 17/3203* (2013.01); *A61B 17/3211* (2013.01); *A61B 34/30* (2016.02); *A61B 17/154* (2013.01); *A61B 2018/00565* (2013.01); *A61B 2018/00601* (2013.01); *A61B 18/20* (2013.01)

(58) Field of Classification Search
  CPC .... A61B 2034/2046; A61B 2034/2055; A61B 2034/2059
  See application file for complete search history.

(56) References Cited

U.S. PATENT DOCUMENTS

| | | | |
|---|---|---|---|
| 5,748,767 A | 5/1998 | Raab | |
| 5,871,018 A | 2/1999 | Delp et al. | |
| 5,876,325 A * | 3/1999 | Mizuno | A61B 34/37 600/117 |
| 6,033,415 A * | 3/2000 | Mittelstadt | G06T 3/02 600/425 |
| 6,205,411 B1 | 3/2001 | Digioia, III et al. | |
| 6,246,200 B1 | 6/2001 | Blumenkranz et al. | |
| 6,322,567 B1 | 11/2001 | Mittelstadt et al. | |
| 6,533,737 B1 | 3/2003 | Brosseau et al. | |
| 6,554,837 B1 | 4/2003 | Hauri et al. | |
| 6,757,582 B2 | 6/2004 | Brisson et al. | |
| 6,788,018 B1 | 9/2004 | Blumenkranz | |
| 6,804,581 B2 | 10/2004 | Wang et al. | |
| 7,035,716 B2 | 4/2006 | Harris et al. | |
| 7,206,626 B2 | 4/2007 | Quaid, III | |
| 7,206,627 B2 | 4/2007 | Abovitz et al. | |
| 7,346,417 B2 | 3/2008 | Lueth et al. | |
| 7,747,311 B2 | 6/2010 | Quaid, III | |
| 7,831,292 B2 | 11/2010 | Quaid et al. | |
| 8,010,180 B2 | 8/2011 | Quaid et al. | |
| 8,095,200 B2 | 1/2012 | Quaid, III | |
| 8,287,522 B2 | 10/2012 | Moses et al. | |
| 8,396,598 B2 | 3/2013 | Sutherland et al. | |
| 8,460,277 B2 | 6/2013 | Suarez et al. | |
| 8,506,555 B2 | 8/2013 | Ruiz | |
| 8,518,051 B2 | 8/2013 | Shoham et al. | |
| 8,838,205 B2 | 9/2014 | Shoham et al. | |
| 8,882,777 B2 | 11/2014 | Heavener et al. | |
| 9,043,023 B2 | 5/2015 | Noro | |
| 9,060,794 B2 | 6/2015 | Kang et al. | |
| 9,119,655 B2 | 9/2015 | Bowling et al. | |
| 9,149,281 B2 | 10/2015 | Bonutti | |
| 9,220,510 B2 | 12/2015 | Cheal et al. | |
| 9,226,796 B2 | 1/2016 | Bowling et al. | |
| 9,271,804 B2 | 3/2016 | Wu | |
| 9,275,192 B2 | 3/2016 | Kang et al. | |
| 9,289,264 B2 | 3/2016 | Iorgulescu et al. | |
| 9,364,291 B2 | 6/2016 | Bellettre et al. | |
| 9,492,237 B2 | 11/2016 | Kang et al. | |
| 9,665,686 B2 | 5/2017 | Van et al. | |
| 9,668,768 B2 | 6/2017 | Piron et al. | |
| 9,724,165 B2 | 8/2017 | Arata et al. | |
| 9,743,936 B2 | 8/2017 | Huet et al. | |
| 9,812,035 B2 | 11/2017 | Stuart et al. | |
| 9,814,468 B2 | 11/2017 | Kang et al. | |
| 9,827,115 B2 | 11/2017 | Walker et al. | |
| 9,901,356 B2 | 2/2018 | Shen et al. | |
| 9,937,014 B2 | 4/2018 | Bowling et al. | |
| 10,004,565 B2 | 6/2018 | Kang et al. | |
| 10,105,149 B2 | 10/2018 | Haider et al. | |
| 10,219,811 B2 | 3/2019 | Haider et al. | |
| 10,383,638 B2 | 8/2019 | Cheal et al. | |
| 10,653,488 B2 | 5/2020 | Kang et al. | |
| 10,709,515 B2 | 7/2020 | Griffiths et al. | |
| 11,129,684 B2 | 9/2021 | Itkowitz et al. | |
| 11,154,369 B2 | 10/2021 | Roldan et al. | |
| 11,278,296 B2 | 3/2022 | Otto et al. | |
| 11,633,233 B2 | 4/2023 | Lavallee et al. | |
| 2005/0171553 A1 | 8/2005 | Schwarz et al. | |
| 2006/0015114 A1 | 1/2006 | Bernardoni et al. | |
| 2006/0142657 A1 * | 6/2006 | Quaid | A61B 90/37 600/424 |
| 2007/0137372 A1 | 6/2007 | Devengenzo et al. | |
| 2007/0156157 A1 | 7/2007 | Nahum et al. | |
| 2008/0010706 A1 * | 1/2008 | Moses | A61B 34/20 600/407 |
| 2009/0228145 A1 | 9/2009 | Hodgson et al. | |
| 2011/0130761 A1 | 6/2011 | Plaskos et al. | |
| 2011/0213384 A1 * | 9/2011 | Jeong | A61B 34/30 606/130 |
| 2013/0096574 A1 * | 4/2013 | Kang | A61B 34/30 606/130 |
| 2013/0144307 A1 * | 6/2013 | Jeong | A61B 90/10 606/130 |
| 2015/0182285 A1 | 7/2015 | Yen et al. | |
| 2015/0257838 A1 * | 9/2015 | Huet | A61B 34/76 901/41 |
| 2016/0113728 A1 | 4/2016 | Piron et al. | |
| 2016/0135816 A1 | 5/2016 | Lavallee et al. | |
| 2016/0206375 A1 | 7/2016 | Abbasi et al. | |
| 2020/0323540 A1 | 10/2020 | Kang et al. | |

FOREIGN PATENT DOCUMENTS

| | | |
|---|---|---|
| CN | 101919736 A | 12/2010 |
| CN | 102778848 A | 11/2012 |
| CN | 103300906 A | 9/2013 |
| CN | 103764061 A | 4/2014 |
| CN | 105050527 A | 11/2015 |
| CN | 105431102 A | 3/2016 |
| CN | 106132335 A | 11/2016 |
| CN | 106132345 A | 11/2016 |
| CN | 110076774 A | 8/2019 |
| DE | 102011004370 A1 | 8/2012 |
| EP | 0456103 A2 | 11/1991 |
| EP | 2529910 A1 | 12/2012 |
| EP | 3007637 A1 | 4/2016 |
| JP | 2009520573 A | 5/2009 |
| JP | 2016523614 A | 8/2016 |
| WO | 2004019785 A2 | 3/2004 |
| WO | 2007045810 A2 | 4/2007 |
| WO | 2007075864 A1 | 7/2007 |
| WO | 2012131658 A1 | 10/2012 |
| WO | 2012131660 A1 | 10/2012 |
| WO | 2014198784 A1 | 12/2014 |
| WO | 2016126914 A1 | 8/2016 |

OTHER PUBLICATIONS

Roth, et al., "A New Less Invasive Approach to Knee Surgery Using a Vision-Guided Manipulator", Virtual Reality, Montpellier, France, Dec. 2000, 8 pages.

Taylor, et al., "An Image-Directed Robotic System for Precise Orthopaedic Surgery", IEEE Transactions on Robotics and Automation, vol. 10, No. 3, Jun. 1994, 15 pages.

* cited by examiner

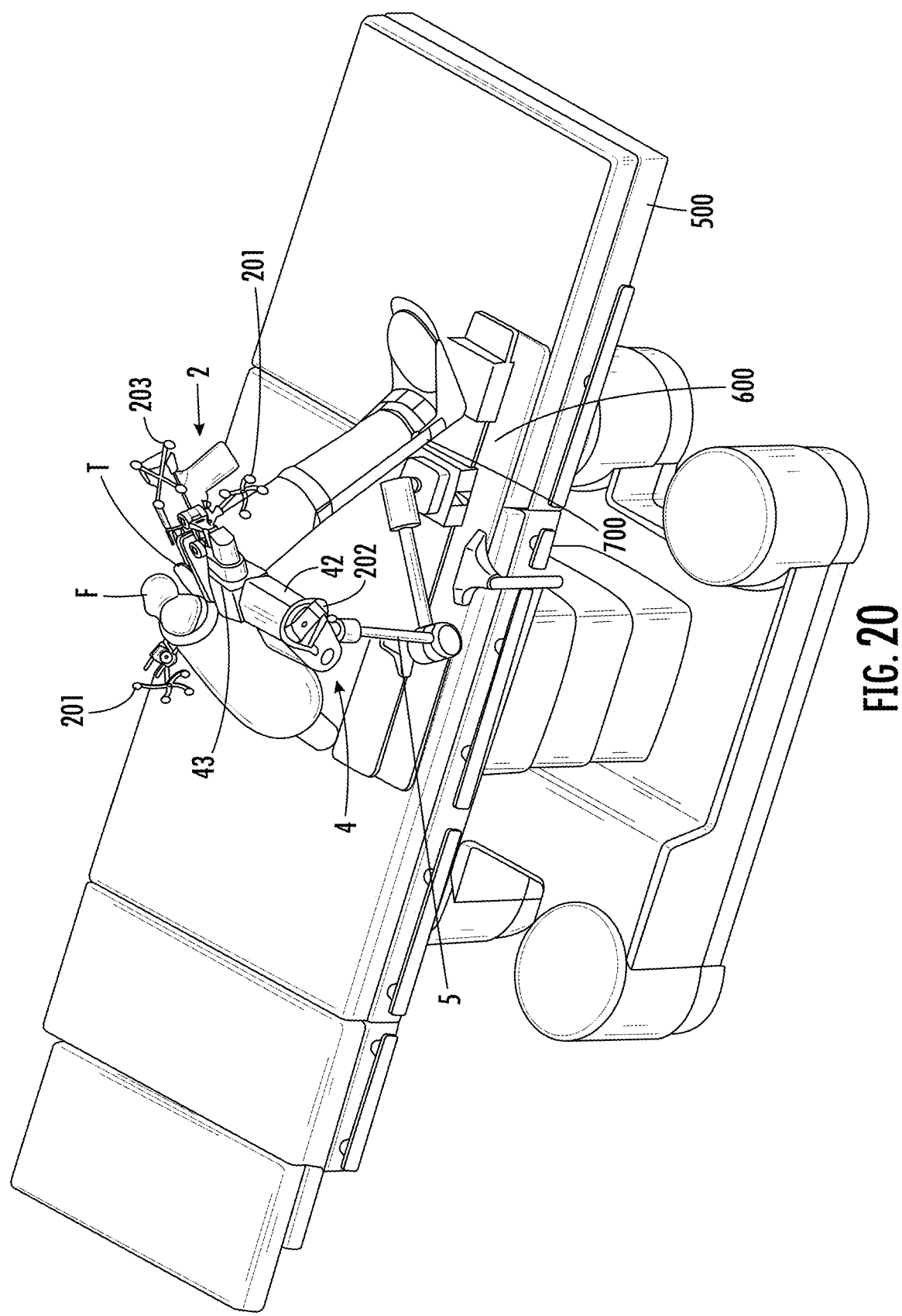

SURGICAL SYSTEM FOR CUTTING AN ANATOMICAL STRUCTURE ACCORDING TO AT LEAST ONE TARGET PLANE

CROSS REFERENCE TO RELATED APPLICATIONS

This application is a continuation of U.S. patent application Ser. No. 16/467,816 (now U.S. Pat. No. 11,974,761, which is the National Stage Entry under 35 U.S.C. § 371 of Patent Cooperation Treaty Application No. PCT/EP2017077370, filed Oct. 25, 2017, which claims priority from European Patent Application No. 16306645.9, filed Dec. 8, 2016, the contents of each of which are hereby incorporated by reference herein in their entireties.

FIELD OF THE INVENTION

The invention relates to a robotic system for cutting an anatomical structure of a patient according to at least one target plane.

BACKGROUND OF THE INVENTION

Total knee arthroplasty typically requires cutting both the femoral epiphysis and tibial epiphysis in order to remove the damaged bone and cartilage and install a knee prosthesis.

To that end, a surgeon has to carry out five or more cuts on the femur and one or more cuts on the tibia by using an oscillating saw through cutting blocks.

FIG. 1 is a schematic perspective view of a knee intended to receive a knee prosthesis including a femoral component FC and a tibial component TC. Generally, the cuts to be made on the femur F are: a distal cut along plane F1, an anterior cut along plane F2, a posterior cut along plane F3, and anterior and posterior chamfers F4, F5 connecting the distal plane and the anterior, respectively posterior, plane. A cut has to be made on the tibia T along plane T1.

In order for the surgeon to carry out all these planes accurately and in a reduced time, computer assisted systems have been developed.

For example, document WO 2014/198784 teaches a surgical system comprising a handheld device that includes:
- a base designed to be held in a user's hand,
- an end-effector for mounting a burr intended to mill a planned volume of a part of a patient's body,
- an actuation unit connected to said base and said end-effector for moving the burr with respect to the base in order to treat said planned volume,
- a support unit connected to the base or to the end-effector which provides a partial mechanical link between the base or the end-effector and the part to be treated.

The system also comprises a tracking unit which is configured to determine in real time the pose of at least one of the burr, the end-effector and the base with respect to the part to be treated.

A control unit of the system is configured to:
(a) compute in real time an optimized path of the burr or of the end-effector with respect to the base depending on said measured pose,
(b) detect whether said computed path of the burr or of the end-effector can be achieved without changing the pose of the base, and, if this is not the case, determine a possible repositioning of the base with respect to the part to be treated,
(c) configure the actuation unit so as to move the end-effector according to said computed path, and
(d) iterate steps (a) to (c) until the planned volume has been treated.

A user interface is used to indicate feedback information to the user.

However, even if the robot described in this document is very efficient for milling a body part, the design with an actuation unit in the form of a planar five-bar linkage as illustrated in document WO 2014/198784 is not optimal for cutting a body part with a saw. Indeed, the degrees of freedom provided by the actuation unit are not suited to the plurality of cutting planes to achieve in knee arthroplasty using a saw mechanism coincident with each plane to be cut.

Document US 2011/0130761 teaches a robotic system dedicated to guiding a saw in order to carry out several cuts on a femur in total knee arthroplasty. The system comprises a navigation system that locates in position and orientation trackers attached to the bone and instruments.

The system comprises a seat rigidly attached to the femur by at least one pin.

An adjustment system comprising two screws is attached to the seat via a ball and socket joint.

The cutting block, which comprises a slot intended to guide a saw blade within a cutting plane, is attached to an arm that supports two motors.

The arm is pivotally mounted on the adjustment system, the orientation of the arm relative to the seat being adjustable by the two screws of the adjustment system.

The arm is rotatable relative to the seat about a first rotation axis by a first motor, the cutting block is rotatable relative to the arm relative to a second rotation axis by the second motor, both rotation axes being parallel to each other.

In use, the seat is rigidly fixed to the femur by the at least one pin, then the position of the first and second rotation axes is modified by the adjustment device which is operated manually by the surgeon, with visual feedback from the navigation system.

Once a suitable position has been found, the trackers attached to the cutting block are removed and the cutting block is no longer navigated.

Then, the motors are operated to move the cutting block about two rotational axes. The surgeon then cuts the bone along each desired cutting plane using a saw received in the cutting block. Thus, the system is not able to detect or compensate in real time a potential misalignment of the cutting block slot relative to the target planes.

A major drawback of such a system is that the rigid fixation of the seat to the femur is quite invasive since it requires implanting large pins into the bone to bear the weight of the robot and compensate for forces exerted during sawing by the saw inserted in the cutting block carried by the robot. Large pins used to carry an important weight and react to important strengths can potentially generate bone fracture. In addition, weight and strengths can lead to motion of the pins in the bone, which will impact significantly the accuracy of the system.

Besides, the rotational axes have to be adjusted very precisely in order to achieve all the target planes. However, this adjustment is difficult and prone to errors or inaccuracy because it is done manually and is only assisted by a visual feedback provided by the navigation system. If the cutting plane slightly moves during sawing because of forces exerted by the user or saw, it would be very difficult for the user to detect it and to correct those adjustments manually.

Moreover, if the pins are not placed in a correct location because of surgical constraints, anatomical constraints, or misuse, the robot will not be able to position the cutting block so that all the cuts can be reached and it will be necessary to reposition the pins in the bone at a slightly different location, which is difficult.

In addition, this system does not allow to carry out the tibial cut while the seat is fixed to the femur, and therefore another specific device is necessary to perform cuts on the tibia, which takes additional time, additional pins, additional systems and efforts.

BRIEF DESCRIPTION OF THE INVENTION

A goal of the invention is to provide a surgical system intended to guide a cutting tool to cut an anatomical bony structure of a patient according to at least one target plane, which does not require any invasive attachment to the patient's bone while controlling precisely the position and orientation of a cutting tool to reach the target plane.

Accordingly, the invention provides a surgical system for cutting an anatomical structure of a patient according to at least one target plane defined in a coordinate system of the anatomical structure, comprising:
(i) a robotic device comprising:
   a cutting tool,
   an actuation unit having a serial architecture comprising from three to five motorized degrees of freedom, at least two of said motorized degrees of freedom being rotational degrees of freedom about respective rotation axes that are substantially orthogonal to each other, configured for adjusting a position and orientation of the cutting tool relative to each target plane,
   a planar mechanism connecting the last segment of the actuation unit to the cutting tool;
(ii) a passive articulated lockable holding arm supporting the actuation unit;
(iii) a tracking unit configured to determine in real time the pose of the cutting plane with respect to the coordinate system of the anatomical structure,
(iv) a control unit configured to determine the pose of the cutting plane with respect to the target plane and to control the actuation unit so as to bring the cutting plane into alignment with the target plane.

In the present text, "substantially orthogonal axes" means that the angle between the axes is 90°±30°.

By "substantially parallel axes" is meant axes making an angle between themselves which is 0°±30°.

By "holding arm" is meant an articulated arm made of at least two segments and that can be locked in a given position. The holding arm is attached to a stable structure of the operating room, such as an operating table, a leg holder, or a mobile cart with blocked wheels.

By "actuation unit" is meant a series of rigid segments linked together by motorized degrees of freedom. The actuation unit is rigidly attached to the extremity of the holding arm. The actuation unit is controlled by a control unit.

By "planar mechanism" is meant a mechanism that constrains an object to move only inside a plane, with at least two degrees of freedom. For example, a planar mechanism can be made of two degrees of translation and one degree of rotation.

By "cutting tool" is meant a saw, a burr, a laser, or a high-pressure water jet, that are able to perform cuts in a bone. For knee surgery, the cutting tool is generally made of a power unit that carries and activates an oscillating saw blade.

By "anatomical structure" is meant in the present text a substantially rigid structure, such as a bone or cartilage, or a joint formed of two or more bones.

By "pose" is meant, in the present text, the 3D position and 3D orientation of a tool in up to six degrees of freedom. It is to be noted that depending on the application, a "pose" may not be necessary determined by all six degrees of freedom but only by one degree of freedom or a subset comprising less than six degrees of freedom.

By "alignment" of the cutting plane with a target plane, is meant in the present text that said cutting plane deviates from the target plane by a distance of less than 1 mm and an angle of less than 1°. Preferably, the cutting plane coincides perfectly with the target plane. To measure such a distance, a selected point of the target plane is projected onto the cutting plane, and the distance between the projected point and the target plane is measured. The selected point shall be in the vicinity of the anatomical structure to be cut. For example, the selected point may be an anatomical point of the anatomical structure, or the center of the anatomical structure to be cut, projected on the target plane.

According to advantageous non-limiting embodiments of the invention, that may be combined whenever appropriate:
   the cutting tool is a surgical saw comprising a saw blade configured to oscillate within a determined cutting plane;
   the cutting plane is parallel to the plane of the planar mechanism;
   the cutting plane is orthogonal to the plane of the planar mechanism;
   the cutting tool is a burr;
   the cutting tool is a laser;
   the cutting tool is a high-pressure waterjet;
   the cutting tool is a scalpel or a lancet adapted for cutting soft tissues;
   the actuation unit comprises three rotational degrees of freedom about successive first, second and third rotation axes;
   the second axis is substantially parallel to the first or to the third axis and the first and third axes are substantially orthogonal to each other;
   the second axis is substantially orthogonal to the first and third axes;
   the actuation unit comprises a first motorized rotational degree of freedom about a first axis, a second motorized translational degree of freedom along a second axis which is substantially orthogonal to the first axis, and a third motorized rotational degree of freedom about a third axis which is substantially orthogonal to the first and second axes;
   the actuation unit comprises a first motorized translational degree of freedom along a first axis, a second motorized translational degree of freedom along a second axis which is substantially orthogonal to the first axis, a third motorized rotational degree of freedom about a third axis which is substantially orthogonal to the first and second axes, and a fourth motorized rotational degree of freedom about a fourth axis (A4) which is substantially orthogonal to the third axis;
   the planar mechanism is passive;
   the planar mechanism is at least partially active;
   the planar mechanism comprises at least two motorized degrees of freedom;
   the system comprises a locking system adapted for locking each degree of freedom of the planar mechanism once the cutting plane has been aligned with the target plane;
   the holding arm comprises a braking system configured to apply a braking force inversely proportional to a distance between a current pose of the robotic device and a target pose enabling alignment of the cutting plane with the target plane;

the tracking unit comprises at least one tracker configured to be rigidly attached to the anatomical structure and at least one tracker rigidly attached to the holding arm and/or to the actuation unit;

the tracking unit further comprises a tracker configured to be rigidly attached to the cutting tool;

the system further comprises an interface configured for attaching the cutting tool at an end of the planar mechanism, wherein the tracking unit comprises a tracker configured to be rigidly attached to said end of the planar mechanism;

the system further comprising a user interface configured to provide feedback information to a user regarding the pose of the robotic device relative to at least one target plane;

the user interface comprises a screen configured to display an indication about whether the cutting plane can be aligned with each target plane with the current pose of the robotic device;

the user interface comprises visual indicators, such as LEDs, arranged on a supporting surface to represent arrows, numbers or letters indicating whether the cutting plane can be aligned with each target plane with the current pose of the robotic device, and/or providing directions to adjust the pose of the robotic device to align the cutting plane with said target plane(s);

the user interface comprises numerical displays that each represents a virtual spirit level, so as to provide feedback information on the orientation of the robotic device;

the system is adapted for performing at least five femoral cuts and one tibial cut in total knee arthroplasty without repositioning the robotic device relative to the anatomical structure;

the system further comprises a support unit configured to provide a partial mechanical link between the anatomical structure and the actuation unit and/or the holding arm;

the support unit comprises at least two detachable elements, a first element configured to be attached to the anatomical structure and a second element configured to be attached to the actuation unit and/or the holding arm;

the first element comprises a strap configured to be wrapped around the anatomical structure and a rigid base comprising at least one slot through which the strap passes, said rigid base being configured to be removably attached to the second element;

the system further comprising at least one soft tissues retractor attached to the first element;

the support unit comprises at least one adjustment mechanism configured for adjusting a distance between the anatomical structure and the actuation unit and/or the holding arm;

the support unit comprises at least one rod configured to be applied onto the anatomical structure;

the support unit comprises at least one suction pad configured to be applied onto the anatomical structure;

the system further comprises an intermediate part removably attached to the actuation unit and/or the holding arm over a sterile drape configured to isolate at least part of the actuation unit and/or holding arm from the patient;

the tracker is rigidly attached to the holding arm and/or the actuation unit via said intermediate part;

the support unit is attached to the holding arm and/or the actuation unit via said intermediate part;

the control unit is configured to allow operation of the cutting tool only when the cutting plane is aligned with the target plane;

the control unit is configured to activate the actuation unit to displace the plane of the planar mechanism in a direction orthogonal to said plane as long as the cutting plane is aligned with the target plane;

the cutting tool rests on the planar mechanism via an interface with complementary features configured to avoid any translation between the cutting tool and the planar mechanism;

the control unit is configured to implement a control loop comprising the following steps:
(S1) determining poses of the actuation unit and the anatomical structure using localization information provided by the tracking unit;
(S2) based on a geometrical model of the actuation unit, computing a theoretical pose of the planar mechanism from the poses determined in step (S1), and computing a deviation between the plane of the planar mechanism and the target plane;
if said deviation is less than a threshold, allowing operation of the cutting tool and returning to step (S1) to determine new poses of the actuation unit and of the anatomical structure;
if said deviation is greater than or equal to said threshold, (S3) projecting the target plane in the coordinate system of the actuation unit;
(S4) computing a new attitude of the actuation unit to align the cutting plane with the target plane, and determining the movements to be applied by the motors of the actuation unit;
(S5) activating the actuation unit to apply said movements, and returning to step (S1) to determine new poses of the actuation unit and of the anatomical structure.

the control unit is configured to implement a control loop comprising the following steps:
(S'1) determining poses of the actuation unit, the cutting tool and the anatomical structure using localization information provided by the tracking unit;
(S'2) computing a deviation between the cutting plane and the target plane;
if the deviation is less than a threshold, allowing operation of the cutting tool and returning to step (S'1) to determine a new pose of the actuation unit, cutting tool and anatomical structure;
if the deviation is greater than or equal to the threshold, projecting (S'3) the cutting plane and the target plane in the coordinate system of the actuation unit,
(S'4) computing a transformation between the plane of the planar mechanism and the cutting plane;
(S'5) updating the target plane with the transformation computed in step (S'4);
(S'6) computing a new attitude of the actuation unit to align the cutting plane with the updated target plane, and determining the movements to be applied by the motors of the actuation unit;
activating the actuation unit to apply said movements.

By "partial mechanical link" is meant a mechanical link between at least two parts, wherein a relative movement of said at least two parts along at least one degree of freedom within a restricted range is possible. This term excludes a "complete" mechanical link, i.e. a link wherein no relative movement between the parts is allowed—an example of such complete mechanical link would be rigidly attaching the robotic system to a bone to be cut by at least one screw or pin implanted into said bone, as in US 2011/0130761 for example. Typically, a partial mechanical link can create damping between the two parts like a spring. Typically, at least one degree of freedom between the two parts is constrained mechanically to a fixed value or to stay in a given range.

By "support unit" is meant a device that creates a partial mechanical link between an anatomical structure and an actuation unit.

As described in further detail below, said partial mechanical link provided between the actuation unit and the anatomical structure of the patient's body may be direct, meaning that the support unit is in contact with the structure to be cut itself (bone), or indirect, meaning that the support unit is in contact with a part of the patient's body adjacent to the structure to be cut. Said adjacent part may consist of a bone belonging to the same joint as the structure to be cut, or of soft tissues (possibly including the skin) that surround said bony structure. An indirect partial mechanical link may be obtained when the support unit connects to the skin of a first bone and the actuation unit is used to cut planes in a second bone connected to the first bone by an anatomical articulation (for example femur and tibia linked by the knee joint). An indirect partial mechanical link may also be obtained when the support unit connects the anatomical structure to an intermediary device and the intermediary device is connected to the actuation unit by a rigid link or by a second partial mechanical link.

Depending on the anatomical part with which the support unit makes contact and on the design of the support unit itself, said partial mechanical link may be rigid (i.e. with a fixed contact point that is not invasive to the bone) or damped.

The device is able to compensate for a given amount of relative pose errors (e.g. due to small movements of the user or involuntary movement of the patient).

The intent of the support unit is to partially stabilize the spatial relationship between the anatomical structure and the actuation unit. Another advantage of the support unit is to constrain the anatomical structure in a well-defined and limited range of motion with respect to the base of the actuation unit. This reduces accidental large motions of the leg during operation of the robot.

While the partial mechanical link allows some slight movements of the robotic device relative to the anatomical structure (due for example to bending of the holding arm, or to involuntary movement of the patient, or to vibrations during the cutting operation), the three motorized degrees of freedom enable taking into account these slight movements to adjust the position of the cutting plane(s) in real time and maintain desired alignment. Thus, as compared with the system described in document US 2011/0130761 which has only two motorized rotational degrees of freedom with parallel axis, the third motorized rotational degree of freedom brought by the invention eliminates the requirement of a very precise, rigid attachment of the seat to the bone and thus reduces the invasiveness of the surgical procedure. Besides, it allows real-time tracking of the cutting plane since the cutting plane is set by three independent degrees of freedom that are motorized and adjusted in real-time.

Advantageously, in the case of knee arthroplasty, the implementation of all the tibial and femoral cuts can be made with the patient's leg in the same position and without substantially moving the system.

BRIEF DESCRIPTION OF THE DRAWINGS

Other features, embodiments and advantages of the invention will be apparent from the detailed description that follows, based on the appended drawings wherein:

FIG. 20 shows a setup of the robotic device according to an embodiment;

DETAILED DESCRIPTION OF EMBODIMENTS OF THE INVENTION

The following description is focused on knee surgery, in particular total knee arthroplasty (TKA), in which case the anatomical structure to be cut is a joint formed of the femur and the tibia.

However, the invention is not limited to this specific application, but can be applied to various applications where there is a need to perform cuts along at least one plane in a bony anatomy. In general, the invention can be used in any surgical intervention requiring at least one osteotomy step. In particular but not limited to, the invention could also be implemented in the following surgical applications: unicompartmental knee arthroplasty (UKA), tibial or femoral osteotomy, patella resurfacing, hallux valgus surgery, hip surgery for cutting the proximal femur, shoulder surgery for cutting the humeral head, spine surgery for correcting deformities and performing an osteotomy of the vertebral body, ankle surgery, maxillofacial surgery.

As will be explained in further detail below, the device is used in a context in which at least one target plane along which the anatomical structure has to be cut is planned before performing the cut(s).

Planning of at least one target plane is performed using patient's pre-operative images (e.g. CT, MRI, Ultrasound images, 2D or 3D X-rays in combination with statistical shape models, PET, etc.) or intra-operative 3D data (e.g. intra-operative CT or CBCT, intra-operative MRI, Ultrasound images, 2D or 3D intra-operative X-ray images, geometric data provided by localizing systems and providing 3D points, clouds of 3D points, surfaces reconstructed from clouds of 3D points, etc.), or both.

Multiple computer-assisted surgery methods exist to register the target plane with a coordinate system attached to the anatomical structure to be cut, using images or geometric patient data collected during surgery.

Typically, intra-operative images or data are used to register pre-operative images in a unique coordinate system attached to the anatomical structure, and usually represented by a tracker that can use any of computer assisted surgery technologies (optical tracker made of reflective markers, optical tracker made of active LEDs, electromagnetic trackers made of coils, combination of inertial sensors, ultrasonic sensors, RFID sensors, etc.).

Using any of these conventional computer-assisted surgery methods results in that the target planes have a known geometric representation in a coordinate system attached to the anatomical structure to be cut, and whose movements are tracked in real-time by a tracking unit as it will be detailed below. Typically, the surgical planning step for total knee surgery results in five target planes defined in a coordinate system attached to a tracker fixed to the femur and one target plane defined in a coordinate system attached to a tracker fixed to the tibia.

Figure 1:
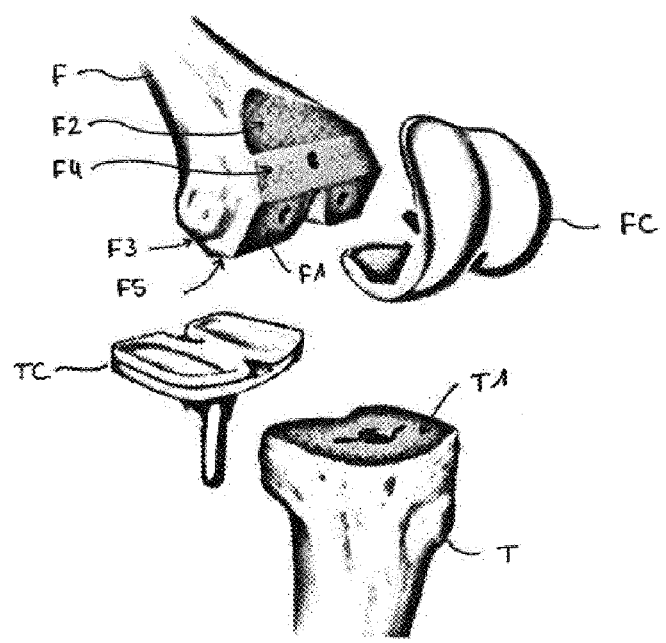
FIG. 1 schematically illustrates the cuts to be made into a femur and a tibia in order to implant a knee prosthesis.
Figure 2:
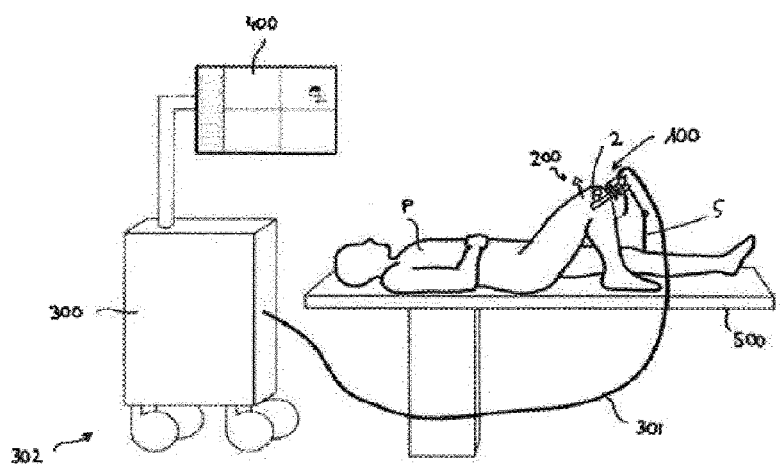
FIG. 2 shows an overview of a surgical system according to the invention.

FIG. 2 shows an overview of a surgical system according to the invention.

A patient P is lying on an operating table 500, e.g. in view of total knee arthroplasty (TKA).

To that end, a cutting tool, such as a saw 2, which is intended to cut the tibial and femoral bones along at least one target plane—preferably, a plurality of target planes—is used by a user such as a surgeon.

The cutting tool is held by the robotic device 100 and is constrained in each target plane by an actuation unit 4 (not shown in FIG. 2, but better seen in subsequent drawings).

The robotic device 100 is connected to a control unit 300 that controls the actuation unit.

Said control unit typically comprises power supply, AC/DC converters, motion controllers to power the motors of the actuation unit, fuses, real-time control system interface circuits.

The system also comprises a tracking unit 200, such that the relative pose of the device and the anatomical structure to be cut is tracked in real time and is shared between a real time control unit and a planning system.

At least one coordinate system is attached to the anatomical structure while at least one coordinate system is attached to the cutting tool and/or the robotic device.

The tracking unit measures the relative motions between both coordinate systems in real time. Real time means high frequencies greater than twenty Hertz, preferably in the range of one hundred to five hundred Hertz, with low latency, ideally less than five milliseconds.

The data obtained by the tracking unit are transferred to the control unit 300 via any suitable connection, with wires 301 or wireless, with low latency.

The real-time control unit is able to carry out the proposed real-time control algorithms at a reasonably high frequency with low additional latency.

The real-time control unit computes in real time the position of the saw with respect to a target plane depending on said measured pose.

In this figure, the connection is represented by a wire 301 but it may instead be wireless if the robotic device is battery-powered.

The control unit and tracking unit may be arranged in a cart 302 that can be moved in the operating room. They can be also mounted on separate carts, articulated holding arms, lighting systems, or the tracking unit can be also mounted directly on the anatomical structure or on some parts attached to the robotic device. For example, the cutting tool can rigidly support an electromagnetic emitter while electromagnetic sensors can be attached to the anatomical structure.

The system may also comprise a visual user interface 400 that is intended to display feedback information to a user and enable system configuration by the user. The feedback information may comprise:

indication about a deviation (distance and/or angle) between the cutting plane and the target plane, before the anatomical structure is cut;

indication about whether the target plane can be achieved with the current position of the robotic device;

directions to reposition the actuation unit with respect to the anatomical structure to be cut in order to allow the actuation unit to align the cutting plane with the target plane; and indication about a deviation (distance and/or angle) between the cutting plane and the target plane, while the anatomical structure is being cut.

Said user interface 400 may advantageously comprise a screen, which may be located on a cart in the operating room, e.g. on the same cart 302 as the control unit and tracking unit, or on a separate cart, or attached to the walls or the celling of the operating room.

In addition to or instead of said screen, the user interface may comprise an indicator that is arranged on the robotic device itself to provide information to the user. Said indicator can be made of LEDs arranged to indicate arrows, numbers or letters, or a miniature display.

A surgical system wherein the control unit, tracking unit and/or user interface are embedded in the robotic device itself would still be within the scope of the invention, provided that the embedded units are powered by a sufficiently powerful power supply or battery and that their size and weight do not hinder the manipulation of the robotic device by the user. For example, micro cameras can be attached to the base of the actuation unit and markers can be attached to the anatomical structure and to the cutting tool.

According to an embodiment, the cutting tool is a surgical saw attached to the actuation unit using a planar mechanism. The saw 2 comprises a casing 23 and a saw blade 22 that oscillates in a determined plane (called "cutting plane") relative to the casing 23 (see in particular FIG. 3A). Thus, the saw blade can be operated to cut the anatomical structure according to a target plane without requiring any cutting block, provided that the actuation unit 4 constrains the saw in the target plane in real time. Usually, the cutting plane is parallel to the longitudinal axis of the casing and the saw blade oscillates on both sides of this axis; such a saw is known in the medical field as a "sagittal saw". The casing is usually positioned relative to the planar mechanism so that the cutting plane is parallel to the plane of the planar mechanism.

According to an embodiment, the saw blade moves back and forth along the longitudinal axis of the casing; such a saw is known in the medical field as a reciprocating saw». The casing is usually positioned relative to the planar mechanism so that the cutting plane is orthogonal to the plane of the planar mechanism.

According to an embodiment (see FIG. 25), the cutting tool is a burr 2'. Indeed, especially if the burr head is small (e.g. with a diameter of the order of three mm), the operation of the burr constrained in a cutting plane allows performing a planar cut. The burr tip can be spherical or cylindrical. Typically a cylindrical shape burr tip with a three mm diameter constrained by the planar mechanism to remain in a plane parallel to the cylinder axis will be rigid enough to make large cuts and small enough to perform fast cutting.

According to an embodiment (not illustrated), the cutting tool is a laser with a system to control the depth of penetration of the laser to avoid damaging soft tissues behind the bone.

According to another embodiment (not illustrated), the cutting tool can be a high-pressure water jet or any other device that creates cuts in an anatomical structure.

According to another embodiment, for cutting soft tissues, the cutting tool can be a scalpel or any electrically activated device such as a lancet.

In the drawings that are described below, the cutting tool is usually a saw, without any intended limitation of the invention.

The actuation unit 4 has a serial architecture made of a plurality of mobile segments. The segments of the actuation unit are numbered 41, 42, 43 throughout the set of drawings. In some embodiments, the actuation unit has three motorized rotational degrees of freedom for adjusting the position and orientation of the cutting plane relative to each target plane. In other embodiments, the actuation unit has two motorized rotational degrees of freedom and one or two motorized translational degrees of freedom. Generally speaking, the actuation unit comprises from three to five motorized degrees of freedom, at least two of which being rotational degrees of freedom orthogonal to each other. In the present text, the term "axis" designates the geometric rotation or translation axis corresponding to said degree of freedom.

The segments and their components are integrated in an optimal way such that the robotic device remains as compact and light as possible while remaining strong enough to be able to hold the planar articulation and the cutting tool, as well as resisting to some normal pressure applied by the user when he/she manipulates the cutting tool.

In the present text, the axes and segments are numbered with increasing numbers starting from the base (i.e. the part of the robotic device that remains stationary while the robotic device works) and towards the cutting tool; this type of numbering is conventional for serial robotic architectures.

Preferably, the architecture of the actuation unit is made of three rotational degrees of freedom.

According to a preferred architecture, the segments are arranged such that the rotation axes of two adjacent segments (i.e. either the first and second axes or the second and third axes) are substantially parallel to each other, and the first axis is substantially orthogonal to the third axis. Preferably, the rotation axes of two adjacent segments are parallel to each other and the first axis is orthogonal to the third axis.

Figure 3A:
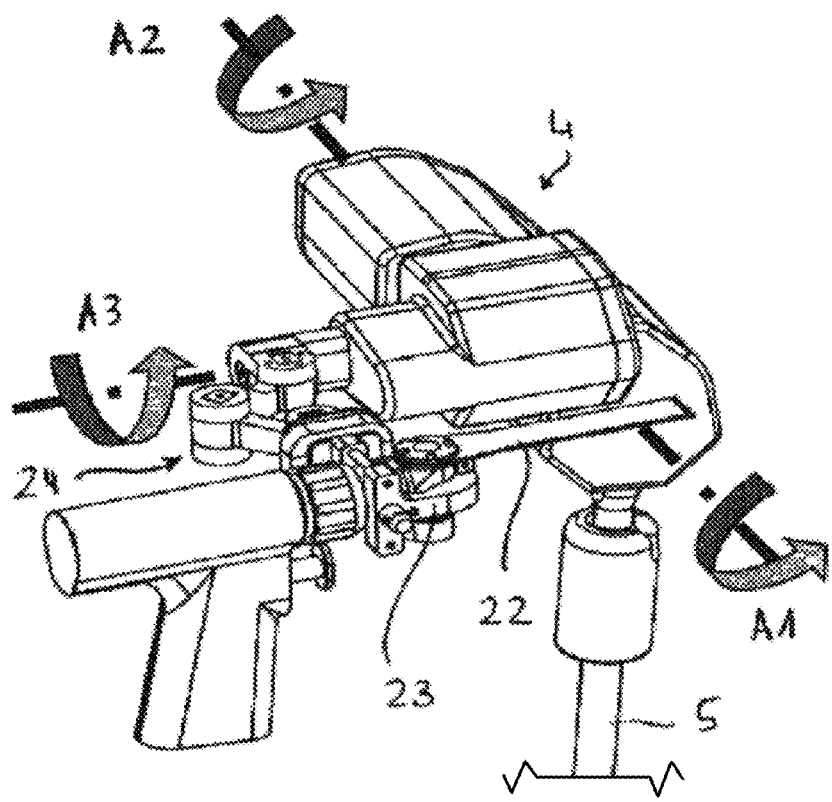
FIGS. 3A and 3B are perspective views of a robotic device according to a first embodiment of the invention.
Figure 3B:
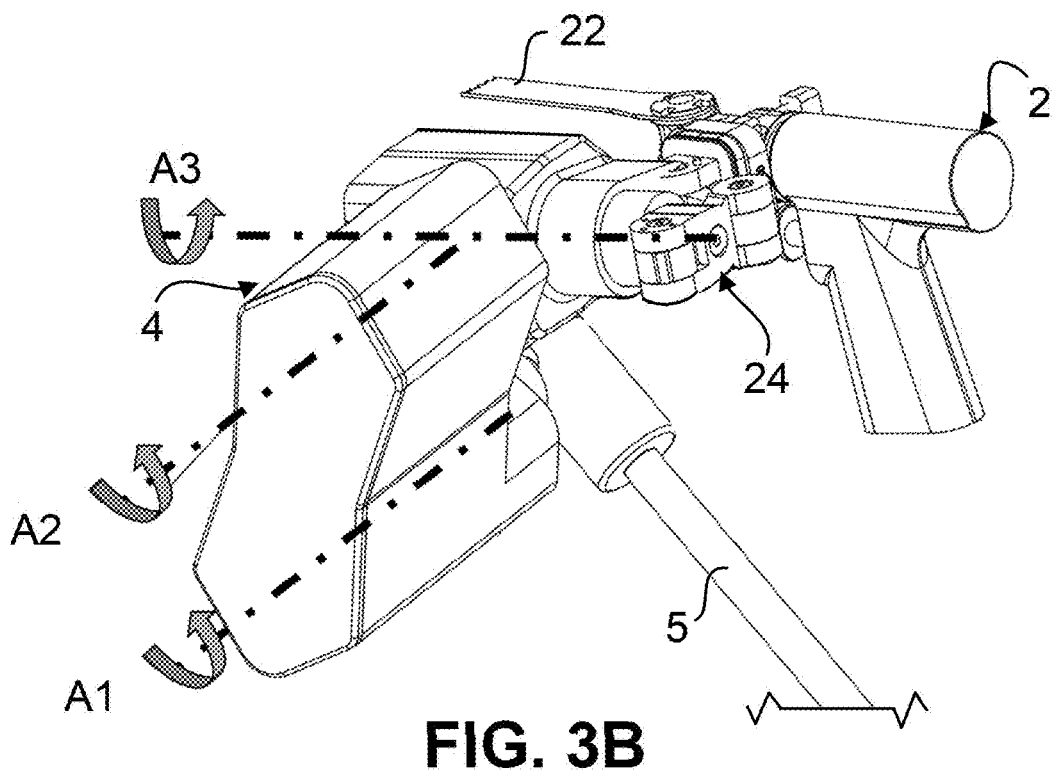

According to a preferred embodiment illustrated in FIGS. 3A-3B, the second axis A2 is parallel to the first axis A1 and the third axis A3 is orthogonal to the first and second axes. Advantageously, the distance between the first axis and the second axis is a fixed distance comprised between 80 and 100 mm. In such case, for application to TKA, the tibial cut and the femoral cuts can be made with a single initial position of the robotic device.

In use for knee arthroplasty (TKA, UKA, etc.), the robotic device may be placed on the medial (internal) or on the lateral (external) side of the leg of interest. The first rotation axis A1 is intended to be substantially orthogonal to the sagittal plane of the knee, and substantially located at the level of the medial or lateral epicondyle. For any application of the robotic device, it is possible to define some anatomical landmarks that are easy to identify and to use them for aligning the actuation unit in a ball park.

Figure 4:
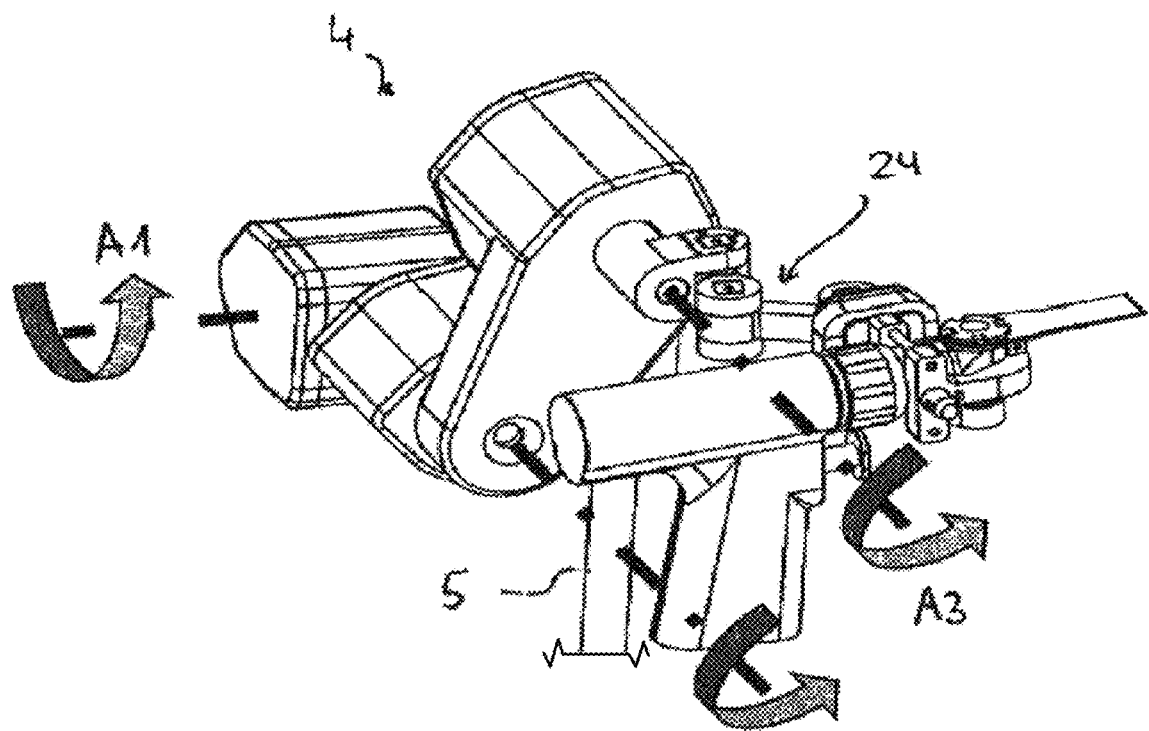
FIG. 4 is a perspective view of a robotic device according to a second embodiment of the invention.

According to an alternative embodiment illustrated in FIG. 4, the second axis A2 is substantially orthogonal to the first axis A1, and the third axis A3 is substantially parallel to the second axis. In a preferred implementation of this embodiment, the second axis A2 is orthogonal to the first axis A1, and the third axis A3 is parallel to the second axis.

In use, the first rotation axis is intended to be substantially parallel to the epicondylar axis of the knee, which is usually substantially parallel to the operating table and orthogonal to the leg axis.

Figure 5:
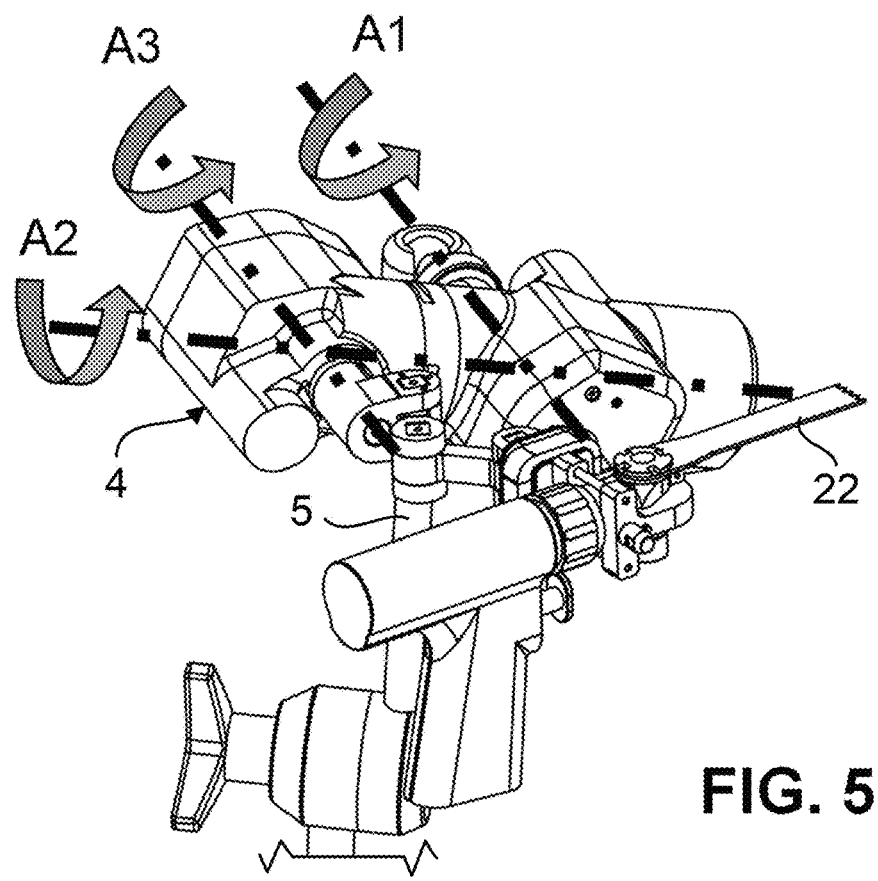
FIG. 5 is a perspective view of a robotic device according to a third embodiment of the invention.

According to another architecture illustrated in FIG. 5, the second axis A2 is substantially orthogonal to the first axis A1 and the third axis A3 is substantially orthogonal to the second axis A2. In a preferred implementation of this architecture, the second axis A2 is orthogonal to the first axis A1 and the third axis A3 is orthogonal to the second axis A2. The first axis A1 and third axis A3 are separated by a fixed distance.

As compared to the architecture of FIG. 5, the architecture of FIGS. 3A-3B has the following advantage: given the intended position of the first rotation axis relative to the knee, this architecture is well conditioned, meaning that small movements of the cutting plane can be achieved by small movements of the actuation unit for all intended target plane positions in the instance of knee arthroplasty procedure.

Advantageously, for application to knee arthroplasty (TKA, UKA, etc.), the dimension of the actuation unit is sufficient to enable performing all the femoral and tibial cuts without substantially moving the robotic device. In this respect, the architecture of FIG. 5 is preferred to the one of FIGS. 3A-3B and FIG. 4 since it provides a greater compacity of the actuation unit. In use, the architecture of FIG. 5 is still well conditioned for knee arthroplasty when the first axis is substantially aligned with the epicondylar axis of the femur.

Figure 6:
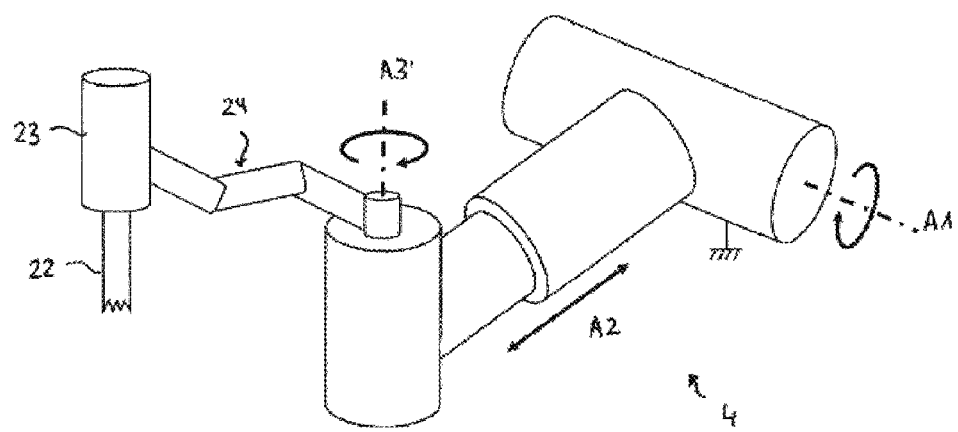
FIG. 6 is a schematic view of the architecture of the actuation unit according to fourth embodiment of the invention.

According to an embodiment illustrated in FIG. 6, the actuation unit 4 comprises two motorized rotational degrees of freedom and one motorized translational degree of freedom, arranged as follows: a first axis A1 which is a rotation axis, a second axis A2 which is a translation axis substantially orthogonal (preferably orthogonal) to A1, and a third axis A3 which is a rotation axis substantially orthogonal (preferably orthogonal) to A1 and A2.

Figure 7:
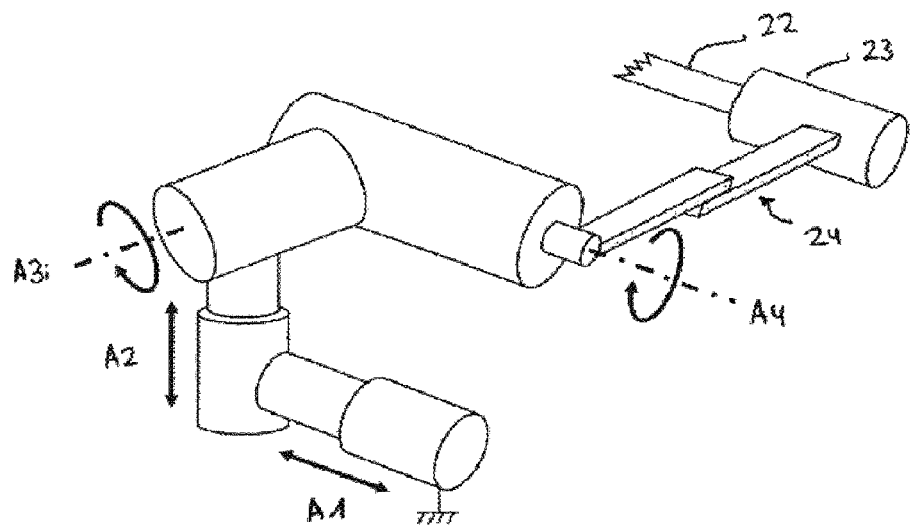
FIG. 7 is a schematic view of the architecture of the actuation unit according to a fifth embodiment of the invention.
Figure 8A:
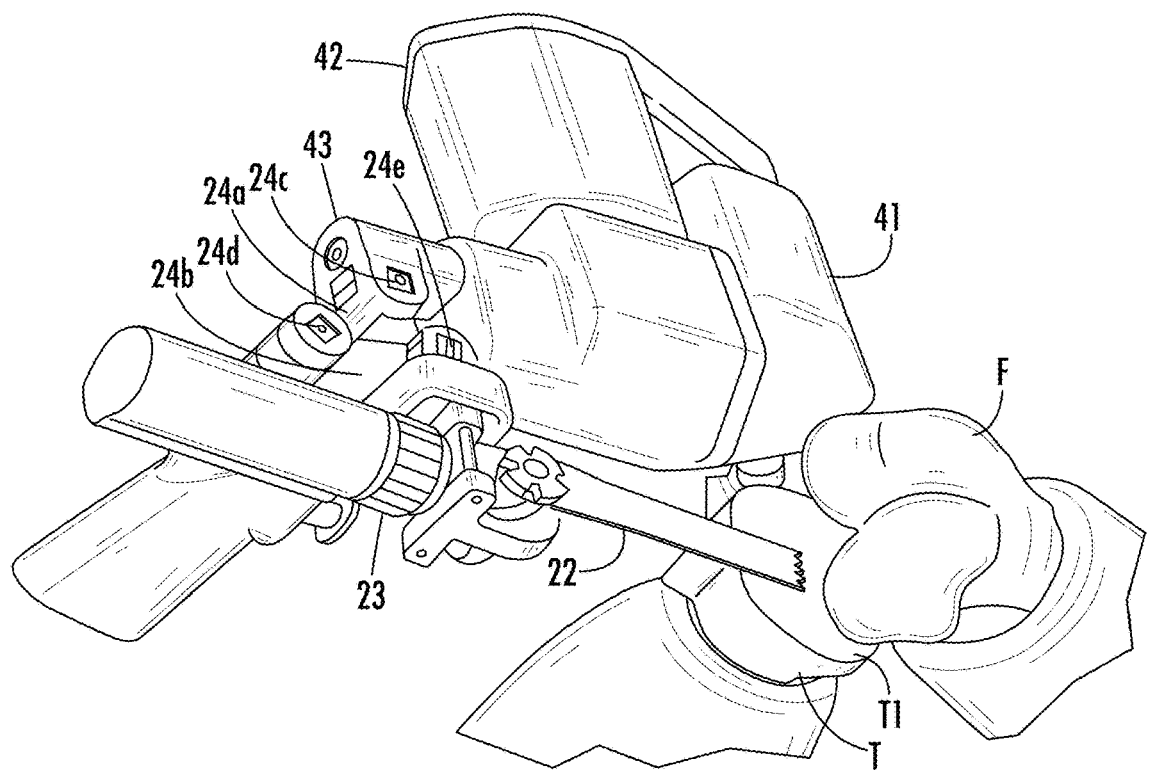
FIGS. 8A-8F show perspective views of a device as shown in FIGS. 3A-3B while carrying out the tibial cut, the distal cut, the anterior cut, the posterior cut, the anterior chamfer cut and the posterior chamfer cut, respectively.
Figure 8B:
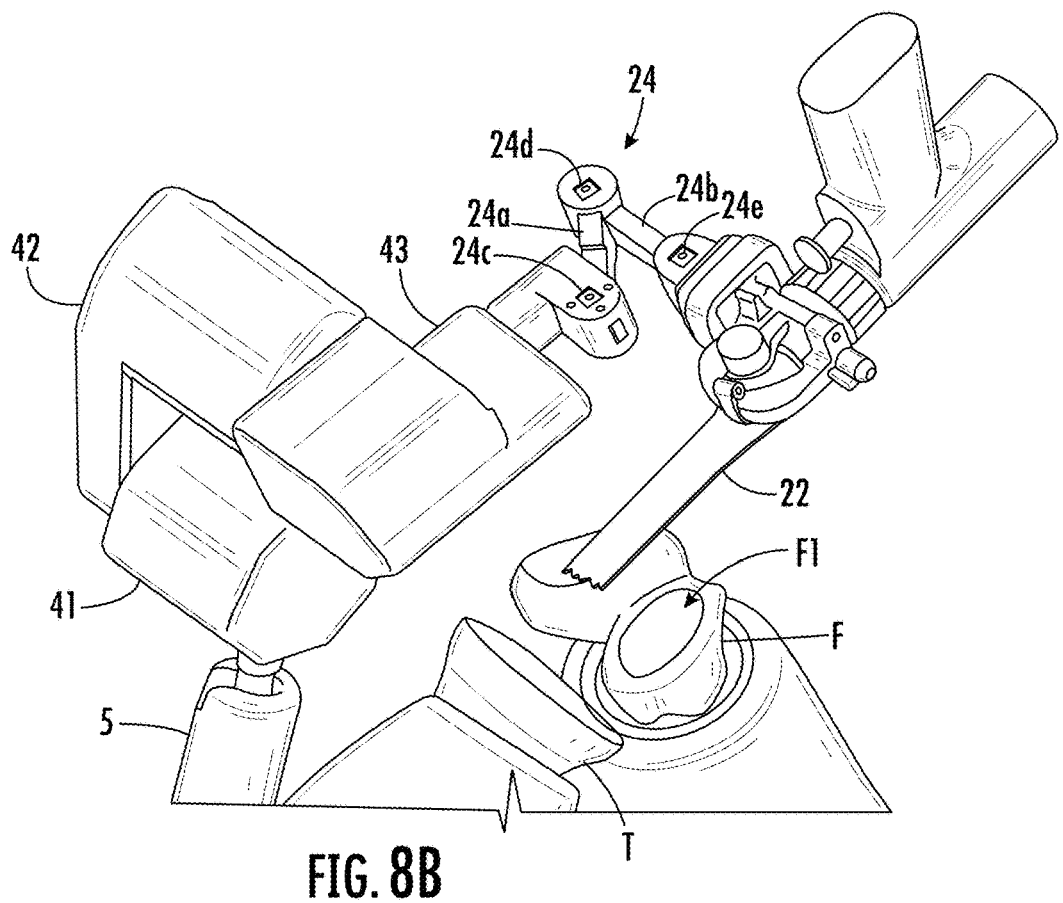
Figure 8C:
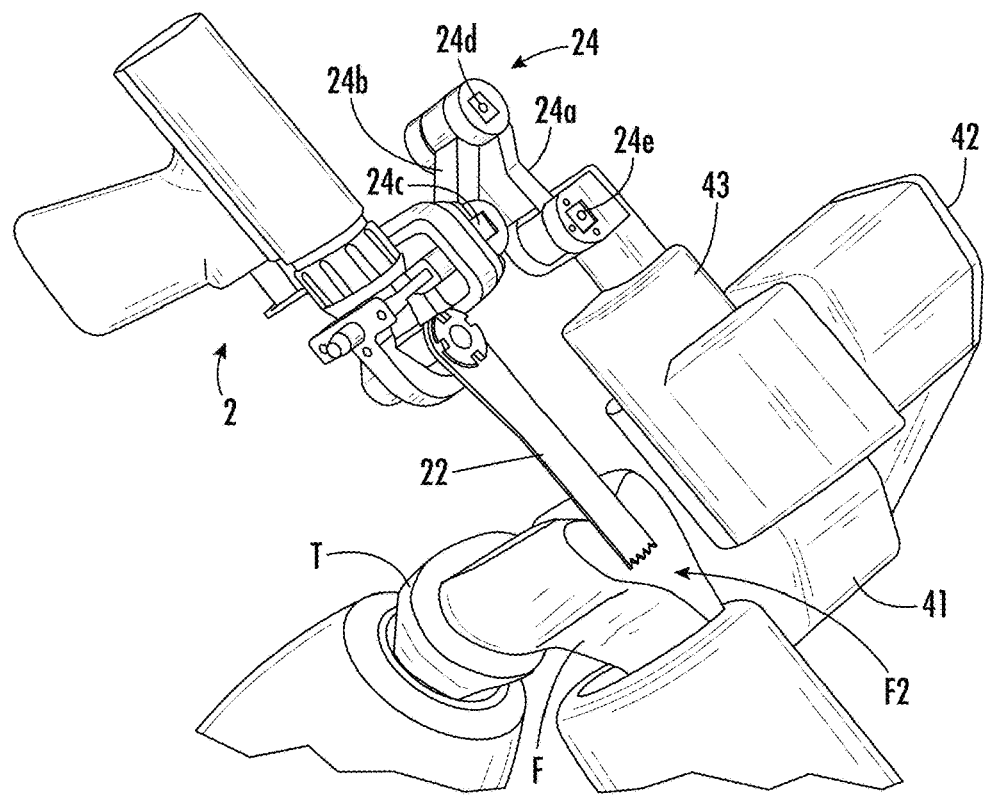
Figure 8D:
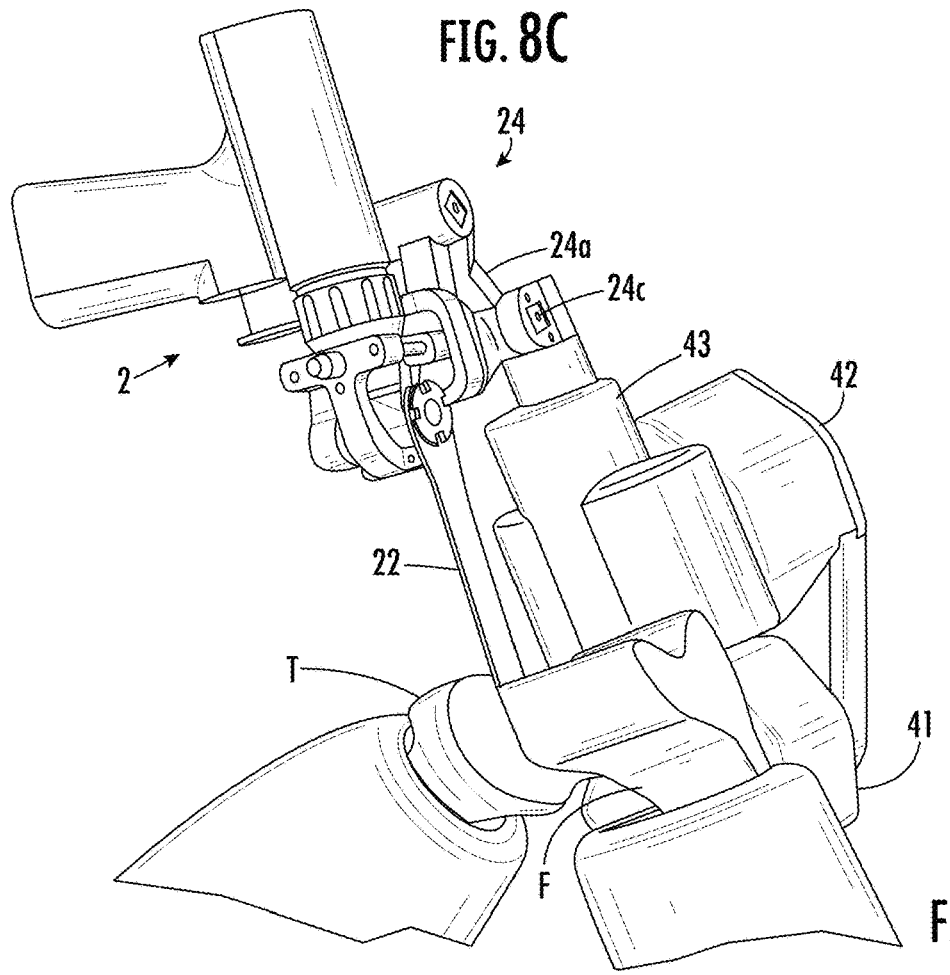
Figure 8E:
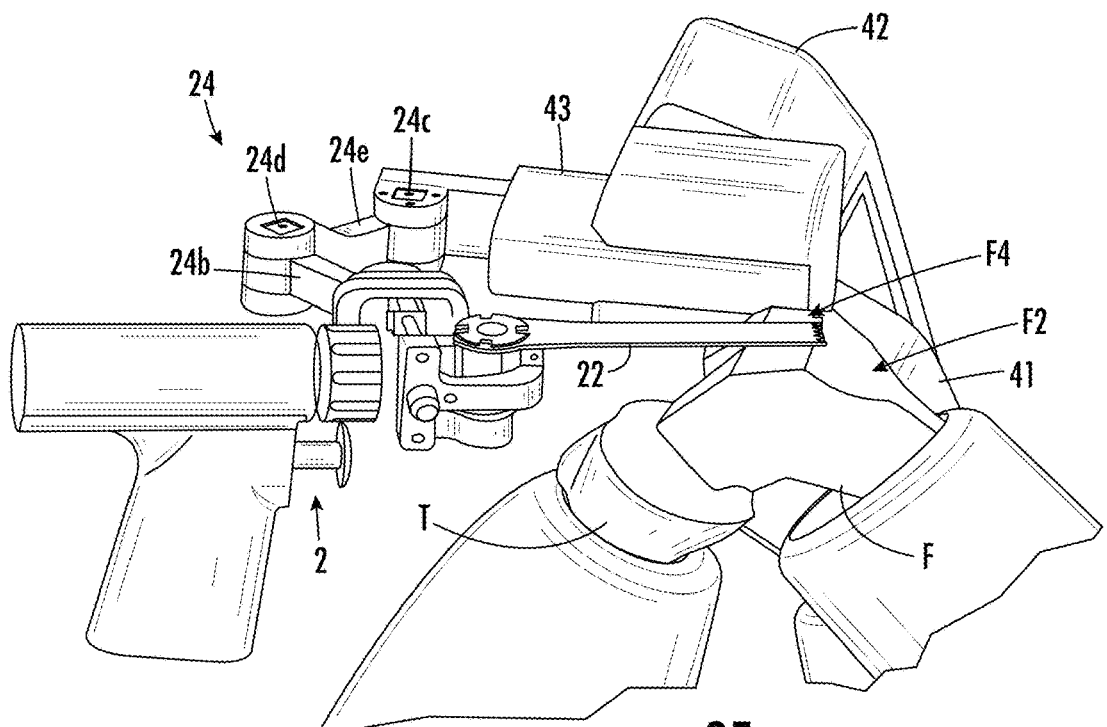
Figure 8F:
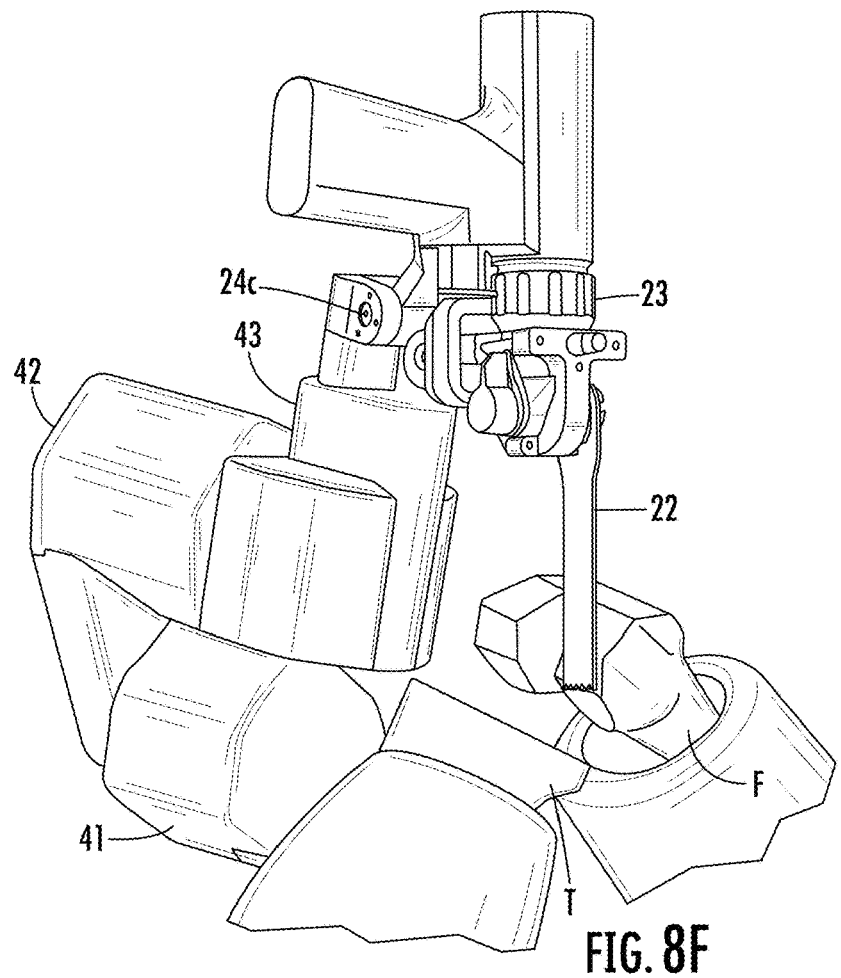

According to an embodiment illustrated in FIG. 7, the actuation unit 4 comprises two motorized rotational degrees of freedom and two motorized translational degrees of freedom, arranged as follows: a first axis A1 which is a translation axis, a second axis A2 which is a translation axis substantially orthogonal (preferably orthogonal) to A1, a third axis A3 which is a rotation axis substantially orthogonal (preferably orthogonal) to A1 and A2, and a fourth axis A4 which is a rotation axis substantially orthogonal (preferably orthogonal) to A3.

In some embodiments, the architecture of the actuation unit may enable additional movements—which can be motorized or not—within the cutting plane. By excluding six motorized degrees of freedom, the invention distinguishes over large surgical robots by a lower inertia— especially according to the first axis—and thus a greater responsiveness required in particular to compensate for bone motion in real time.

As it will be explained in more details below, the actuation unit 4 is controlled by the control unit 300. The control unit may be integrated in the robotic device, or remote from the robotic device.

The cutting tool is coupled to the actuation unit by a planar mechanism designated under reference 24 throughout the set of drawings, the planar mechanism being configured to constrain the movement of the cutting tool within the cutting plane.

Advantageously, the cutting tool can be decoupled from the planar mechanism. Preferably, especially in the case where the cutting tool is not intended to receive a tracker, the attachment means for the cutting tool provides reproducible fixation.

Several different architectures exist to implement a planar mechanism. For example, the planar mechanism can be made of only one rotation axis and then one translation axis that carries the cutting tool along its longitudinal direction. Alternatively, the planar mechanism can be made of two orthogonal translation axes and then a rotational axis. According to another embodiment, the planar mechanism can be a slider in the form of an arch, including a rotation axis, and then a translation axis that carries the cutting tool.

According to an embodiment, the planar mechanism 24 is passive, meaning that the mechanism is not motorized and can be freely manipulated by the user. For example, in the embodiment shown in FIGS. 8A-8F, the passive mechanism 24 comprises segments 24a-24d linked by three parallel rotation axes 24e-24g which are orthogonal to the cutting plane. One advantage of such a passive mechanism is to preserve all the perceptions of the user when the saw is manipulated in the bone. For example, surgeons are used to freely manipulate a saw in a cutting block and to detect when the saw blade has reached the back of the bone by sensing changes in the bone resistance, and this perception is fully preserved with a passive planar mechanism that has very low friction at its joints.

Figure 26:
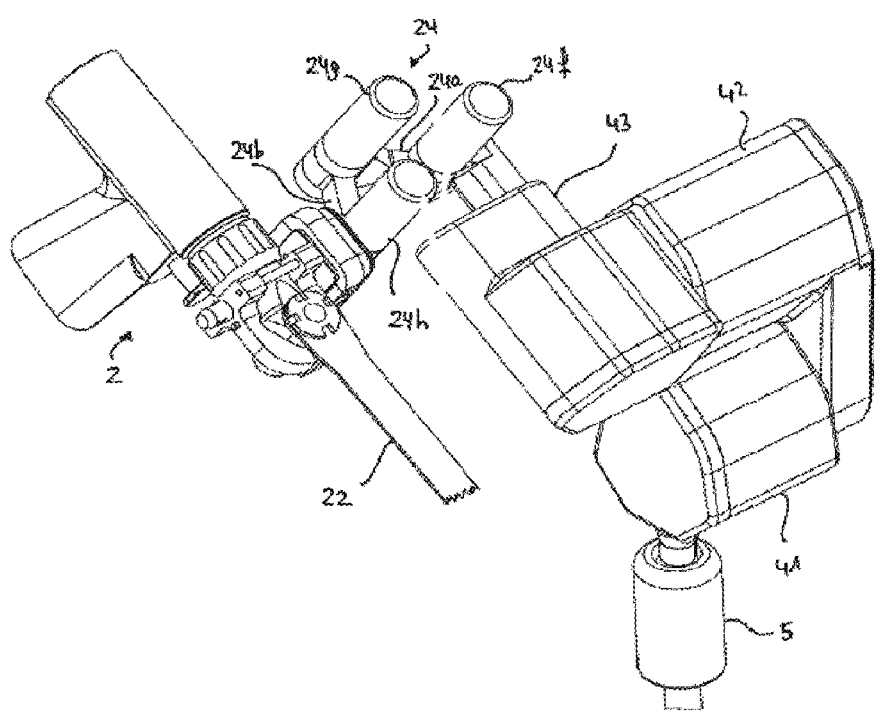
FIG. 26 shows an embodiment of a motorized planar mechanism.

Alternatively, the planar mechanism may also be at least partially active, i.e. comprising at least one motorized degree of freedom. If the planar mechanism is active, i.e. it comprises at least two motorized degrees of freedom (see FIG. 26), the cut(s) can be performed automatically. It is to be noted that said motorized degrees of freedom are all configured to move the cutting tool within the cutting plane.

Whatever the embodiment, the planar mechanism may comprise a locking system for locking each of its degrees of freedom once the cutting plane has been aligned with the target plane.

It is possible to make the actuation unit and planar mechanism sterile components, to be sterilized before each intervention. But, in a preferred embodiment, the actuation unit with its cables and equipped with the planar mechanism are covered by a single-use sterile drape. Additional components of the system can be also protected under the sterile drape. This has the advantage of facilitating and reducing cost of manufacturing and design, but also of being used easily for multiple consecutive surgeries without requiring re-sterilization of the device. The cutting tool itself is sterile, like any conventional surgical tool. Typically, it is sterilized before each intervention using autoclave. Different types of mechanical adaptors between the sterile drape and the cutting tool can be provided. Such adaptor does not require a very precise reproducible fixation if the saw contains a tracking element (described in more detail below), which increases the accuracy of the global system. The sterile drape covers the planar mechanism to facilitate the design and manufacturing of the device. For example, this design allows the use of ball-bearings mechanisms that would be difficult to autoclave.

The system comprises an articulated lockable holding arm 5 supporting the actuation unit and suited to be connected to a mechanical support such as an operating table, a leg holder or mounted on a mobile cart which wheels can be blocked. A leg holder is an adjustable mechanism configured to maintain the leg in a given flexed position when the patient lies on the operating table.

The holding arm 5 is made of several articulated segments using ball-and-socket joints, rotational and/or translational joints.

The holding arm is lockable, either manually by a knob (mechanical locking system) or actively by a dedicated actuator of a locking system. The locking system may be an electrical system, a piezoelectric system, a hydraulic system, a pneumatic system or a combination of such systems (e.g. a hydraulic cylinder driven by an electric motor). For example, company SMITH & NEPHEW sells a passive holding arm, actively lockable, named SPIDER™. The actuator can be a button, a foot switch, a remote button, etc. To manipulate the robotic device, the user has to maintain the actuator activated until the desired pose of the robotic device has been achieved.

The holding arm supports the weight of the robotic device and maintains it in a rough positioning relative to the anatomical structure to be treated. It limits the movements of the user when operating the device—and, in advantageous embodiments, also damps movements of the user and/or the patient, vibrations of the cutting tool and reaction forces caused by movements of the actuation unit.

According to an embodiment, the holding arm is passive.

Advantageously, the holding arm may be braked progressively depending on the distance between the robotic device and a target position of the robotic device relative to a tracker fixed to the patient. For example, the braking force may be inversely proportional to the distance of the robotic device to its target position. Alternatively, one or several concentric volumes (e.g. cubes or spheres) may be defined around the target position of the robotic device. The braking force may adjust depending on the presence of the robotic device in one of said volumes. Thus, when the robotic device is close to the target position, the holding arm is braked and the user may receive a force-feedback information. Alternatively, feedback information may be provided in the form of a light or acoustic signal. For example, a variable flash frequency and/or intensity of a light signal may indicate the distance between the robotic device and its target position. Similarly, a variable frequency, repeat speed and/or amplitude of an acoustic signal may indicate such a distance. In any case, the braking is not full, so that the user is always able to manipulate the robotic device until its final desired position. The holding arm is then locked upon an action from the user (e.g. by operating the actuator, e.g. releasing or pushing a button). If the user wants to move the robotic device again, he/she has to operate the actuator again, which frees the holding arm—possibly with a braking force as described above. If a new target position of the robotic device is defined, new braking volumes are defined, and the braking is adjusted based on said new volumes.

In an embodiment, the holding arm is equipped with weights to counterbalance the weight of the control unit, as it is commonly used for carrying and placing microscopes in the surgical field for example.

In an embodiment, the holding arm has a vertical translation with a spring mechanism to compensate for the weight of the global system, then it has a serial architecture with a large planar structure made of three parallel and vertical axes. Each axis is equipped with a locking system.

Figure 9:
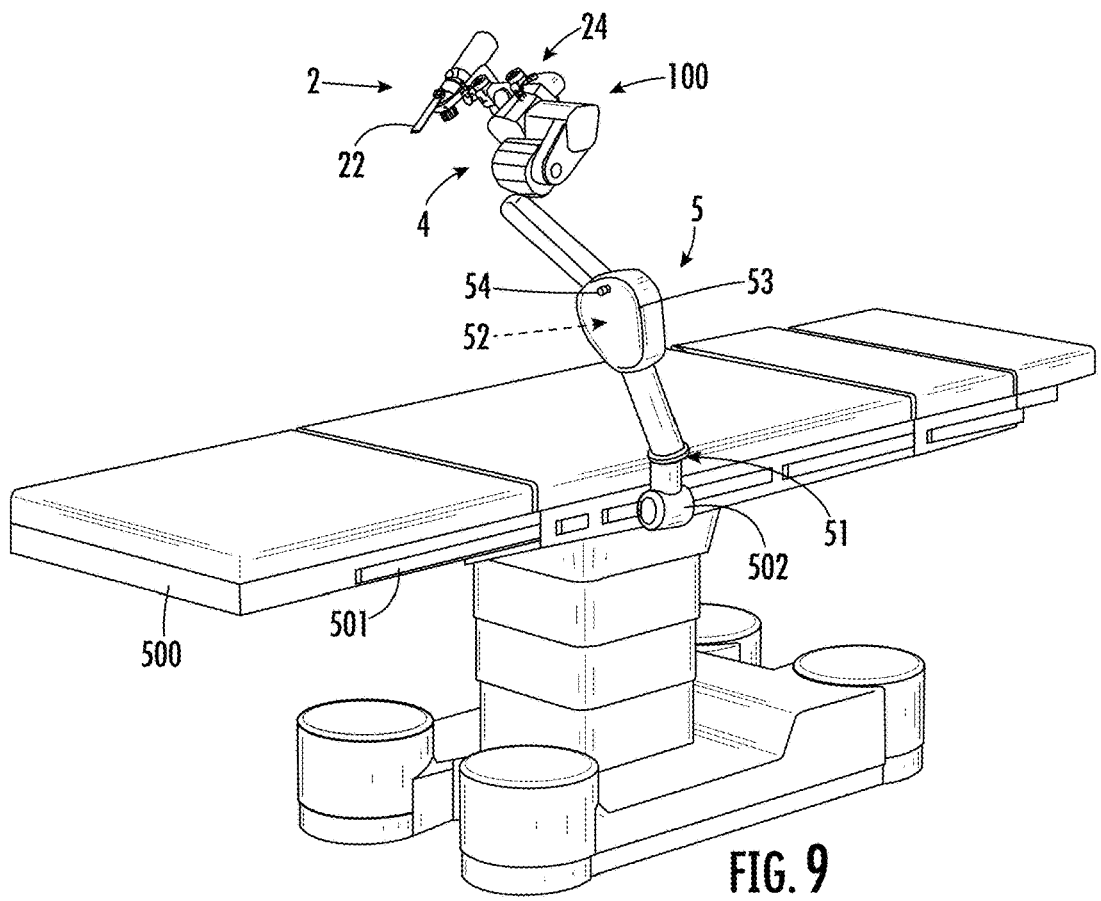
FIG. 9 illustrates an embodiment of the holding arm.

FIG. 9 illustrates an embodiment of the holding arm 5, which is fixed to a rail 501 of the operating table 500 by a clamp 502. The holding arm is formed of the following kinematic links, in a sequence starting from the clamp: a pivot link 51 and a ball joint 52. The central module 53 is provided with an actuator 54 that allows unlocking the holding arm when pushed. Alternatively, such an actuator could be arranged on a higher part of the holding arm so as to manipulate the arm and the robotic device easily in case the user wants to change the position of the robotic device relative to the anatomical structure.

Figure 10:
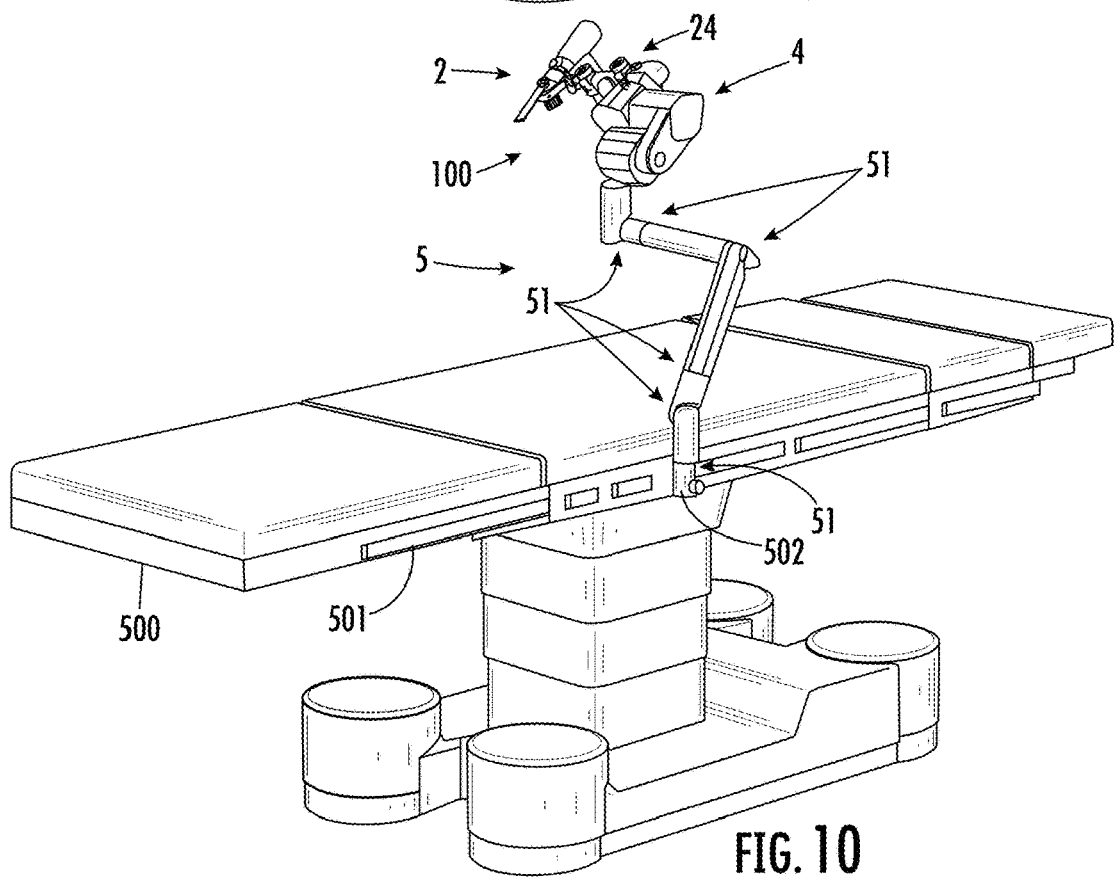
FIG. 10 illustrates another embodiment of the holding arm.

FIG. 10 illustrates another embodiment of the holding arm 5, which is fixed to a rail of the operating table 500 by a clamp 501. The holding arm is formed of six pivot links 51. The holding arm may be locked by an actuator (not shown).

Preferably, the connection between the holding arm and the actuation unit is as close as possible to the first segment of the actuation unit or to the center of gravity of the robotic device in order to minimize any lever-arm effect. The part of the actuation unit that is attached to the holding arm is called the base of the robotic device.

According to an embodiment, the first segment of the actuation unit may be fixed relative to the holding arm. In such case, the second segment of the actuation unit is necessarily mobile relative to the first segment. This architecture is advantageous in that it minimizes the weight of the moving components of the actuation unit. As a result, the robotic device may be more responsive, which is favorable to real time control of the cutting plane.

According to an embodiment, the first segment of the actuation unit may be mobile relative to the holding arm. In such case, the first and second segments are preferably embedded in a single housing.

Figure 11:
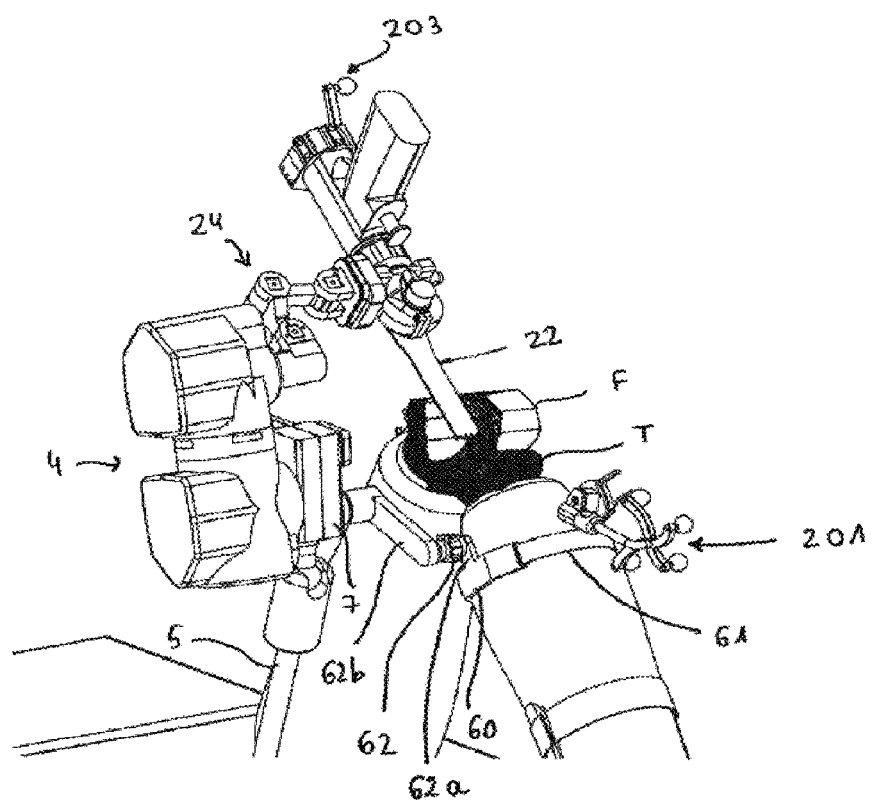
FIG. 11 illustrates an embodiment of a support unit attached to the tibia.

According to an embodiment, the device may further comprise a support unit configured to create a partial mechanical link between the actuation unit and the anatomical structure. The support unit may be attached directly or indirectly to the holding arm or to the actuation unit. In the latter case, the support unit may be attached to a fixed segment of the actuation unit (e.g. the first segment if it is fixed to the holding arm) or to a mobile segment of the actuation unit (freely rotatable about the axis of rotation of the segment relative to the holding arm). According to an embodiment that will be described below with reference to FIGS. 11 and 12, the support unit 6 may be attached to an intermediate part 7 removably attached to the holding arm 5 or to the actuation unit 4. This intermediate part 7 can be for example a sterile part to be placed over the sterile drape (not shown) to create a sterile connection between the support unit 6 and the holding arm or the actuation unit. The support unit is usually a sterile component. The connection between the support unit and the actuation unit or the holding arm can be established on the sterile drape via the intermediate part if the actuation unit is covered with a sterile drape. In case the robotic device is sterile, the support unit can be connected directly to the robotic device.

According to an embodiment, the support unit comprises at least one element intended to make contact with the anatomical structure to be cut or an area of the patient's body adjacent to the anatomical structure to be cut so as to provide a partial mechanical link between the actuation unit and the anatomical structure.

If a support unit is used, it is arranged so as not to hinder the movements required to carry out the surgical intervention. In particular, the support unit is arranged so as not to interfere with the movements of the robotic device to implement each cut.

Generally, the support unit comprises at least one element intended to be in contact with an anatomical structure (the anatomical structure to be cut or an anatomical structure adjacent thereto, e.g. the soft tissues surrounding a bone to be cut). This element 60 can be attached to the patient by at least one strap 61. To that end, this element may comprise at least one slot through which the strap extends. The strap can be flexible or semi-rigid (e.g. like fastening device for ski boots). The strap can be adjusted by any suitable means, such as fastening mechanisms, hoop-and-loop fasteners (also known as Velcro™) etc. Alternatively, the strap can be adhesive, or comprises at least one portion made of a high-friction coefficient material (e.g. soft thermoplastic, silicone) placed in contact with the anatomical structure.

Besides, the support unit 6 comprises a mechanical connection 62 between the base of the actuation unit (or the holding arm or the above-mentioned intermediate part) and the element of the support unit which is in contact with the anatomical structure. The connection can be activated when the robot is in use and deactivated when the surgeon needs to move the leg. According to an embodiment, said connection may be rigid. Alternatively, said connection can be articulated and lockable in at least one degree of freedom to adjust the distance between the robotic device and the patient, or to take into account the patient's morphology. Once the robotic device has been placed in the desired position and orientation, some degrees of freedom may remain free, provided that the support unit still allows limiting movements and vibrations of the anatomical structure relative to the actuation unit. This mechanical connection 62 may be made of at least two parts 62a, 62b detachable from one another, for example using a rapid fixation, latch or magnets. A first part 62a is attached to the element 60 of the support unit in contact with the anatomical structure; a second part 62b is attached to the base of the actuation unit or to the holding arm or to the above-mentioned intermediate part. Thus, the intermediate part, the actuation unit or the holding arm may be disconnected from the anatomical structure simply by releasing the mechanical connection, without any need to dismount the support unit from the patient. This is particularly useful in case the user wants to change the position or flexion of the leg during the intervention, e.g. in view of checking the ligament balancing or the postoperative alignment of the leg.

Figure 31A:
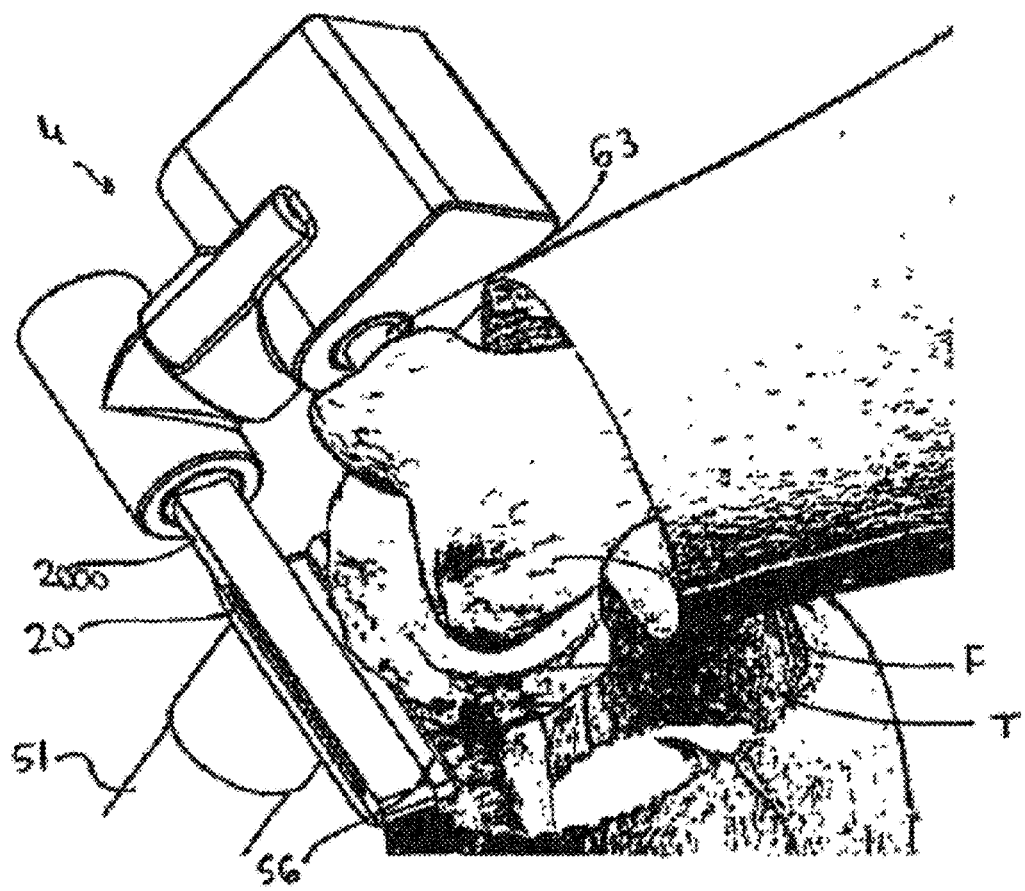
FIGS. 31A-31B show various embodiments of the support unit of the device.
Figure 31B:
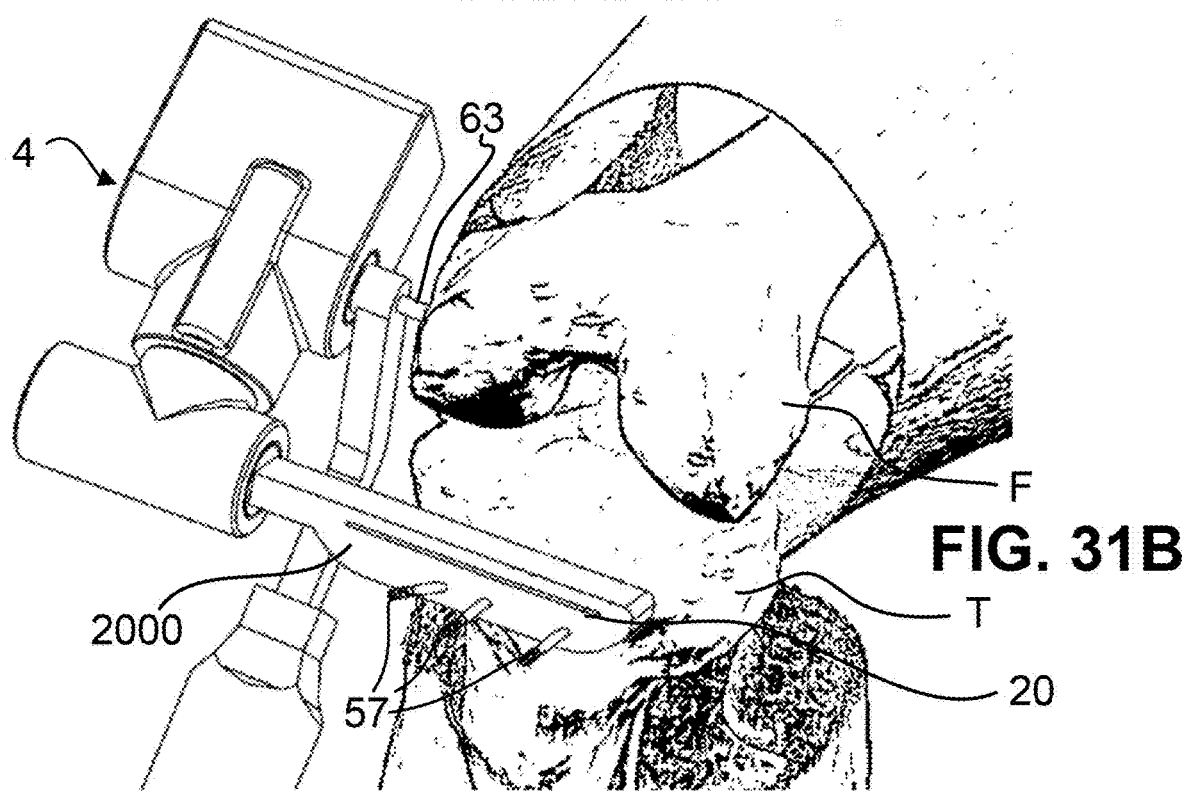

Optionally, the support unit may include, in combination with the above described components, one or several rods 63 intended to be in contact with the anatomical structure (see FIGS. 31A-31B). For example, in the case of TKA, such a rod could be in contact with the epicondyle. Said rod can be rigid or damped (using a spring member). Thus, without being rigidly attached to the bone, said rod allows maintaining a distance between the anatomical structure and the robotic device when the above-described strap is tightened in a determined direction.

In addition to or instead of the rod(s), the support unit may comprise at least one (active or passive) suction pad intended to stay in place on an anatomical structure (bone, skin or other soft tissue) in case of relative movement of the robotic device and the anatomical structure, and also to provide damping.

In a preferred embodiment, the support unit is attached around the leg.

Figure 12:
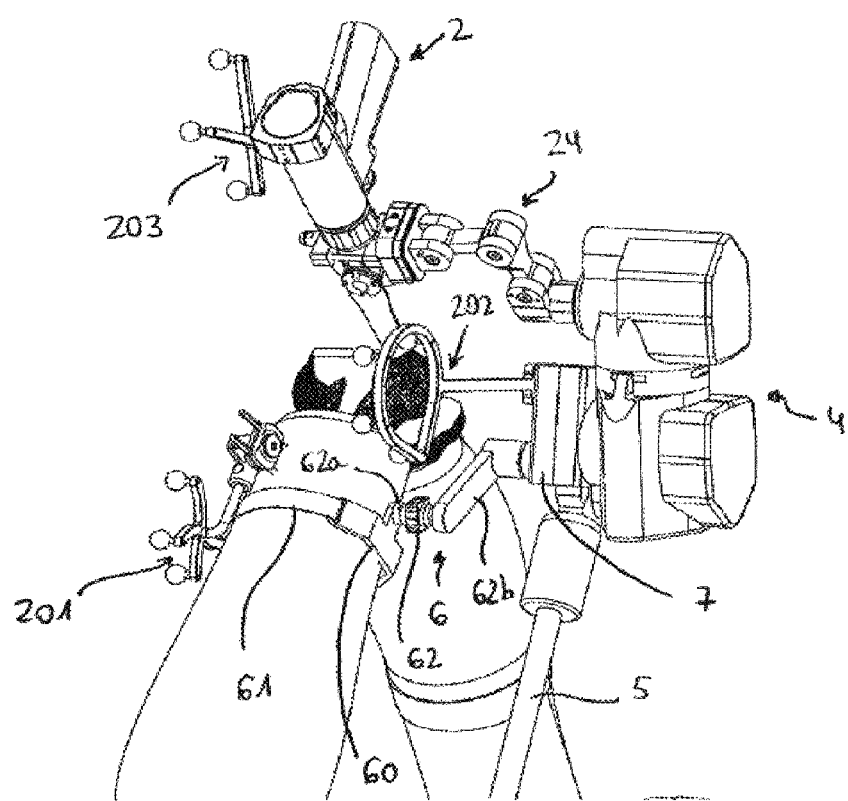
FIG. 12 illustrates an embodiment of a support unit attached to the femur.

The support unit may be attached to the tibia (see FIG. 11) or to the femur (see FIG. 12). The support unit may also be attached to both the tibia and the femur; in this case, the support unit is advantageously articulated so as to enable moving the leg (in particular adjusting the flexion of the leg) without removing the support unit.

According to an embodiment, retractors are attached to the support unit. Said retractors are pulling the soft tissues to offer a large incision and vision to the surgeon. A first retractor can be attached to the medial side of the incision and to the back part of the support unit using a link that can be tensioned. A second retractor can be attached to the lateral side of the incision and to the back part of the support unit using a link that can be tensioned. During maneuvers of the leg, the support unit is detached from the actuation unit basis or holding arm or intermediate part, using a fast but strong mechanical connection.

Figure 13:
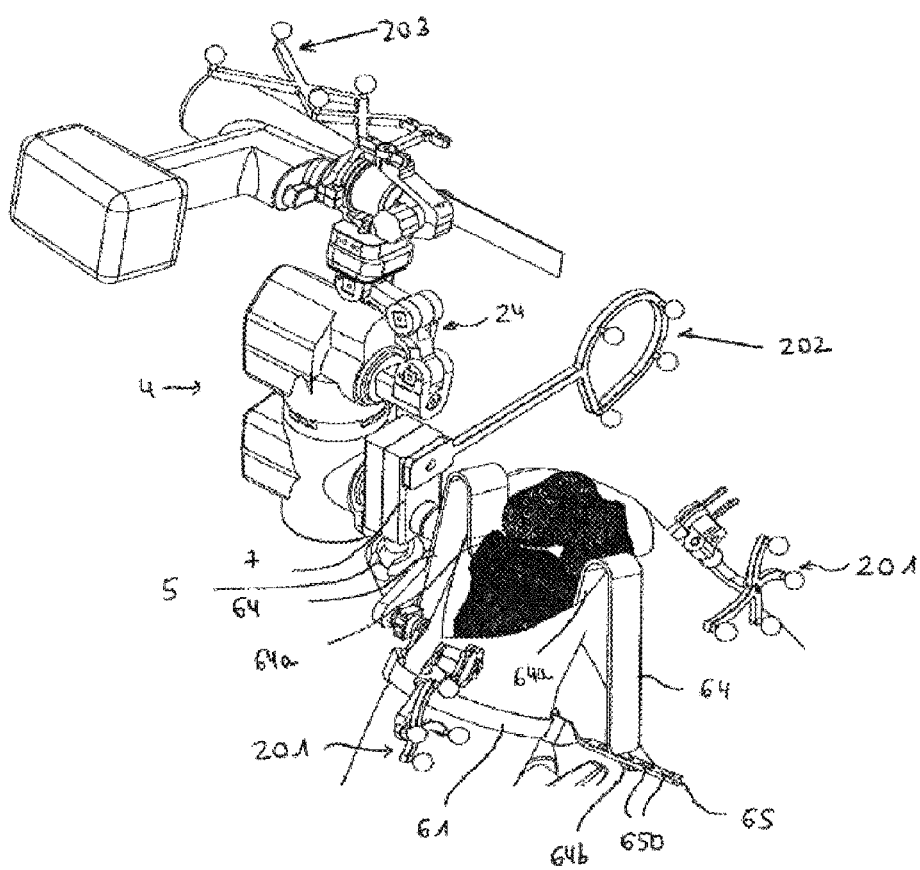
FIG. 13 illustrates an embodiment of a support unit supporting soft tissues retractors.

FIG. 13 illustrates one embodiment of retractors attached to the support unit.

The support unit 6 is attached to an intermediate part 7 that is itself removably attached to the holding arm 5. In particular, the intermediate part 7 allows making a sterile connection with the holding arm 5 over the sterile drape (not shown). The intermediate part 7 may advantageously carry a tracker 202. The support unit 6 comprises a strap 61 supporting a base 61 from which extends a first fastener 62a, and a connecting member comprising a second fastener 62b cooperating with the first fastener to create a fast and strong connector 62, the connecting member being attached to the intermediate part.

Each retractor 64 has a bent shape, with a first end 64a configured to make contact with the anatomical structure and a second end 64b configured to be attached to the strap 61 of the support unit. More precisely, two bars 65 comprise a slot through which the strap 61 passes, so that the bars 65 are maintained in a direction projecting away from the leg. Each bar comprises a plurality of holes 650. The second end 64b of each retractor is inserted into a selected hole 650 of the respective bar 65 such that the first end 64a of the retractor bears against the anatomical structure and sufficiently pulls the soft tissues.

Figure 14:
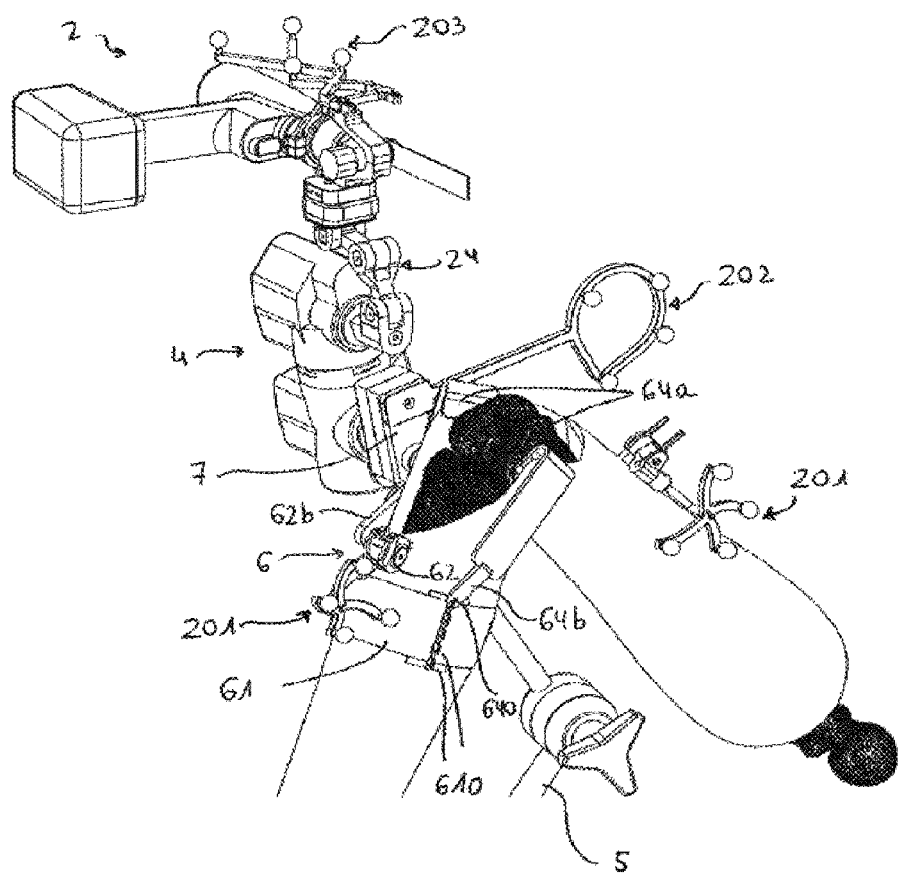
FIG. 14 illustrates another embodiment of a support unit supporting soft tissues retractors.

FIG. 14 illustrates another embodiment of retractors attached to the support unit.

The support unit 6 is attached to an intermediate part 7 that is itself removably attached to the holding arm 5. In particular, the intermediate part 7 allows making a sterile connection with the holding arm 5 over the sterile drape (not shown). The intermediate part 7 may advantageously carry a tracker. The support unit 6 comprises a strap 60 supporting a base from which extends a first fastener, and a connecting member comprising a second fastener cooperating with the first fastener to create a fast and strong connector 62, the connecting member being attached to the intermediate part.

Each retractor 64 has a bent shape, with a first end 64a configured to grip the soft tissues and a second end 64b configured to be attached to the strap 61 of the support unit. More precisely, the strap 61 may be wider than in FIG. 13 and comprises a plurality of hooks 610 on its two sides. The second end 64b of each retractor comprises a hole 640. This hole 640 is coupled with a selected hook 610 of the strap such that the first end 64a of the retractor sufficiently pulls the soft tissues.

Attaching the retractors to the support unit is particularly advantageous in that the retractors need not to be held by the surgeon's assistant, which saves space in the vicinity of the incision.

The support unit acts as a stabilizer. Said support unit may be rigid, damped (e.g. spring-loaded) and/or provide adjustable damping properties. The contact between the support unit and the patient's body may be made of one or several points or of at least one surface.

Before cutting the anatomical structure, the user plans the intervention on the planning system, based on pre-operative and/or intra-operative medical images and data.

This planning step allows determining each target plane suited to perform the cut of the anatomical structure. It is specific to each application.

Figure 15:
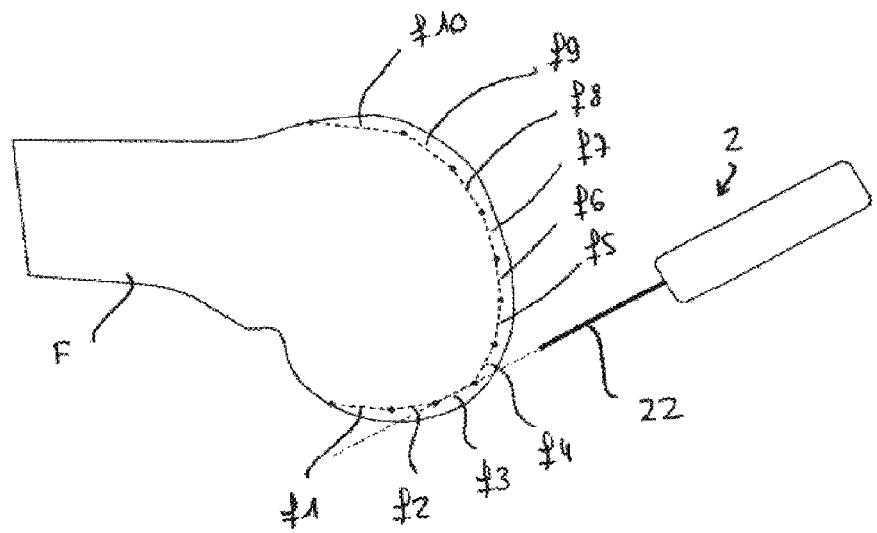
FIG. 15 schematically illustrates an embodiment with ten target planes to be cut on the femur using a robotic device according to the invention.

For example, as already described above, in the case of TKA, planning the implantation of a prosthesis on a knee usually results in the definition of five target planes on the femur and one on the tibia. It is also possible to define more than five cutting planes for fixing a prosthesis to a bone in order to optimize the shape of the prosthesis based on individual anatomy for example. This is illustrated in FIG. 15 wherein ten cutting planes f1-f10 are defined to fit the patient's anatomical structure on a sagittal view of a femur. It is particularly advantageous to use the robotic device according to the present invention for such bone preparation, to enable to quickly perform many cuts with high accuracy.

The planning system may form part of the surgical system according to the invention; otherwise, the planning system may be provided separately and connected to the control unit.

During the surgical intervention, the user may either use preoperative data/images together with intra-operative registration methods, or use directly intraoperative data/images. In both cases, the result of the planning consists of at least one target plane, the pose of each plane being determined in the coordinate system of the anatomical structure to be cut.

The pose of each target plane is then transferred to the control unit.

The control unit initializes its sub-systems and the device is ready to use.

Before starting the device, the articulated holding arm is moved by a user so as to bring the actuation unit in a rough suitable position relative to the anatomical structure, and is then locked. Then, the cutting tool is attached to the planar mechanism.

In case a support unit is also used, the support unit is connected to the anatomical structure to be cut or to an adjacent region of the patient's body to provide a partial mechanical link between the actuation unit and the anatomical structure. The partial mechanical link provided by the support unit enables the user to make small movements to reposition the device, or enables the robotic device to compensate for involuntary motion of the patient. No additional invasive action (e.g. implantation of pins) on the patient is required.

Once operation of the device has been started by the user, the tracking unit continuously feeds back tracking information to the control unit for recalculation and visualization purposes.

In addition, the user interface provides information to the user about the ability to align the cutting plane with the target plane in the current device position and, if appropriate, gives indications on how to reposition the device appropriately.

The system also comprises a tracking unit 200 configured to determine in real time the pose of the saw with respect to the anatomical structure to be cut.

The tracking unit may typically comprise a tracking system, which is known per se.

Tracking systems commonly used in computer-assisted surgery use a variety of different technologies (passive optical, active optical, electromagnetic, inertia with gyroscopic measurements, ultrasonic, etc.) that can be used individually or in combination. According to a preferred embodiment, the tracking system is based on passive optical technology.

The tracking unit comprises at least one tracker that may be attached to any component of the actuation unit, e.g. to one of the mobile segments.

The position of each segment of the actuation unit is known in real time thanks to encoders or sensors of the motors, and a calibrated model of the robot that includes all axes and distances of the robot segments. Using this model, and well-known geometric modeling techniques in robotics, it is possible to calculate the relative positions of all segments, so if one measurement is known in a coordinate system attached to the robot basis using an external tracker, then any segment position is also known in the same coordinate system. Additionally, if a tracker is attached to the base of the actuation unit and a second tracker is attached to the anatomical structure, then the pose of any segment of the actuation unit is known in the coordinate system attached to the tracker of the anatomical structure.

According to an embodiment, no tracker is attached to the cutting tool. In this way, the cutting tool does not bear the weight of the tracker and the region of operation of the cutting tool is freed from the tracker.

However, if the planar mechanism coupling the cutting tool to the actuation unit is passive, only the pose of the plane of the planar mechanism and of the connection between the planar mechanism and the last segment of the actuation unit can be determined. In other words, the pose of the saw itself relative to the actuation unit cannot be precisely known. Note that this problem may be avoided with an active planar mechanism that comprises encoders, since the position of each segment of the active planar mechanism and of the saw can thus be determined.

In another and preferred embodiment, a first tracker is attached to the first or second segment of the actuation unit and a second tracker is attached to the cutting tool in order to offer a redundant and more accurate measurement of the cutting tool position and orientation for safety purpose, taking into account any mechanical backlash that may exist between the actuation unit and the cutting tool.

In addition, at least one tracker is rigidly attached to the patient's anatomical structure to be cut so as to allow localizing the cutting plane relative to the coordinate system of this anatomical structure to be cut.

Throughout the set of drawings, a tracker attached to the anatomical structure is designated by reference 201, a tracker attached to the actuation unit or to the holding arm is designated by reference 202, and a tracker attached to the cutting tool is designated by reference 203.

In case no tracker is attached to the cutting tool, the compensation of relative motion between the robotic device and the anatomical structure may be implemented as follows.

During the cut, the actuation unit displaces the planar mechanism so that the cutting plane coincides with the target plane. The pose of the robotic device is updated at a high frequency, considering the positions of the base of the robotic device and the anatomical structure.

To that end, if the cutting plane is parallel to the plane of the planar mechanism, one solution is to use the geometrical model of the robotic device to determine the new position of the actuation unit (motors) that would make the plane in which the planar mechanism moves and the target plane coincide. Said geometrical model may be known from the CAD model of the actuation unit, or from a dedicated calibration step, using well known geometric modeling techniques in robotics.

Figure 16:
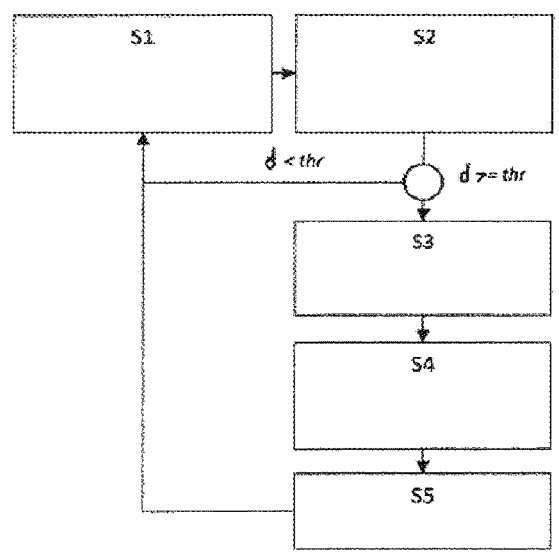
FIG. 16 represents an embodiment of a compensation control loop implemented by the control unit, in case no tracker is attached to the cutting tool.

FIG. 16 is a flowchart describing the control loop allowing the compensation.

In step S1, a new pose of the robotic device and the anatomical structure is determined using localization information provided by the trackers.

In step S2, based on the geometrical model of the robotic device, the theoretical position and orientation of the planar mechanism can be computed from the new pose determined in step S1. Then, a deviation d between the plane of the planar mechanism and the target plane is computed.

If the deviation d is less than a threshold thr, the cutting tool can be operated and a new pose of the robotic device and anatomical structure is determined (step S1).

If the deviation d is greater than or equal to the threshold thr, then in step S3 the target plane is projected in the coordinate system of the robotic device.

In step S4, a new attitude of the robotic device is computed to reach the target plane. This computation determines the movements to be applied by the motors of the actuation unit.

In step S5, the motors of the actuation unit are activated in accordance with step S4.

Then, the new position of the robotic device and anatomical structure is determined (step S1).

However, this procedure relies solely on the geometrical model of the robotic device, which is never perfect due to mechanical backlashes and irregularities, as well as structural deformations that are changing depending on the relative positions of the cutting tool and the various parts of the robotic device.

Another issue is that the planar mechanism itself may slightly bend. As a result, its components do not have the same position and orientation. Indeed, a variable shift on the position and orientation of the planar mechanism is observed, and the compensation of the cutting tool position is never perfect, preventing the robotic device from converging to the target plane. In such case, either the robotic device oscillates, or it converges to a position which is shifted from the target plane.

To improve the motion compensation, an additional tracker may be rigidly attached to the cutting tool. This additional tracker allows determining reliably the position and orientation of the cutting tool in the coordinate system of the robotic device.

Instead of attaching said additional tracker to the cutting tool, it is possible to rigidly attach it to the end of the planar mechanism opposite the actuation unit. Said end of the planar mechanism may comprise an interface capable of receiving any type of cutting tool as mentioned above (sagittal saw, reciprocal saw, burr . . . ) but also other surgical tools such as a drill guide to be used to drill the pegs for implanting the prosthesis, and/or a cutting guide, etc. For example, the drill guide can have a toothed end intended to grip into the surface of the anatomical structure where a hole has to be drilled. Advantageously, a handle is provided at the opposite end of the drill guide to facilitate its manipulation by the surgeon. Thus, once the toothed end has been applied to the anatomical structure, the surgeon can simply change the orientation of the drill guide thanks to a navigation interface. The drill may carry a tracker, instead of having the tracker carried by the end of the planar mechanism.

The compensation of relative motion between the robotic device and the anatomical structure using the additional tracker rigidly attached to the cutting tool or to the end of the planar mechanism may be implemented as follows.

The control loop described with reference to FIG. 16 is thus changed to the control loop shown in FIG. 17.

In the improved control loop, the actual position of the cutting tool or of the end of the planar mechanism is used instead of the theoretical position of the planar mechanism.

This greatly increases the confidence in the compensation mechanism.

Moreover, the association of the tracker attached to the cutting tool and the tracker attached to the actuation unit enables dynamic estimation of the alignment error between the two. This alignment error is then used to correct the position and orientation of the planar mechanism to the target plane.

Figure 17:
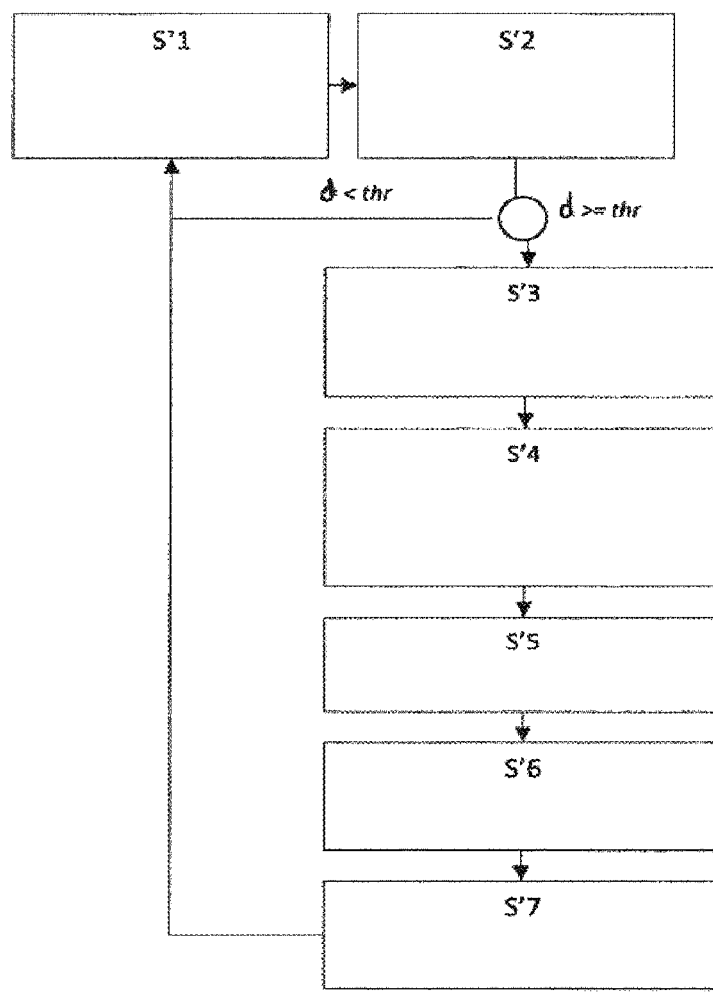
FIG. 17 represents another embodiment of a compensation control loop implemented by the control unit, in case a tracker is attached to the cutting tool.

FIG. 17 is a flowchart describing the control loop allowing the compensation.

In step S'1, new poses of the robotic device, the cutting tool and the anatomical structure are determined using localization information provided by the trackers.

In step S'2, a deviation d between the plane of the cutting tool (cutting plane) and the target plane is computed.

If the deviation d is less than a threshold thr, the cutting tool can be operated and a new pose of the robotic device and anatomical structure is determined (step S'1).

If the deviation d is greater than or equal to the threshold thr, then in step S'3 the plane of the cutting tool (cutting plane) and the target plane are projected in the coordinate system of the robotic device.

In step S'4, a correction matrix $T_{err}$ corresponding to a rigid transformation between the plane of the planar mechanism and the plane of the cutting tool is computed.

In step S'5, the target plane is updated with $T_{err}$.

In step S'6, a new attitude of the robotic device is computed to reach the target plane. This computation determines the movements to be applied by the motors of the actuation unit.

In step S'7, the motors of the actuation unit are activated in accordance with step S'6.

Then, the new position of the robotic device and anatomical structure is determined (step S'1).

From this base algorithm, further improvements have proven to enhance the behavior of the robotic device:
  spatially filtering the positions of the various elements (for instance thanks to a Kalman filter or equivalent);
  averaging the estimation of $T_{err}$ in a given time frame, for instance thanks to quaternion averaging techniques. This allows reducing the potential oscillations due to small inconsistencies between the transformation estimation and the more complex reality of the mechanical links.

The correction matrix $T_{err}$ may vary depending on the current extension of the planar mechanism and therefore it is not constant. It also depends on the mechanical backlash and flexion of the planar mechanism, the position of the robot, and other factors. The correction matrix is calculated in real time, such that the deviation of $T_{err}$ between two calculations is not significant, considering reasonable motions of the saw by the user. This method of correction is extremely precise and efficient for compensating any mechanical defects, backlash and errors in the model.

Figure 18:
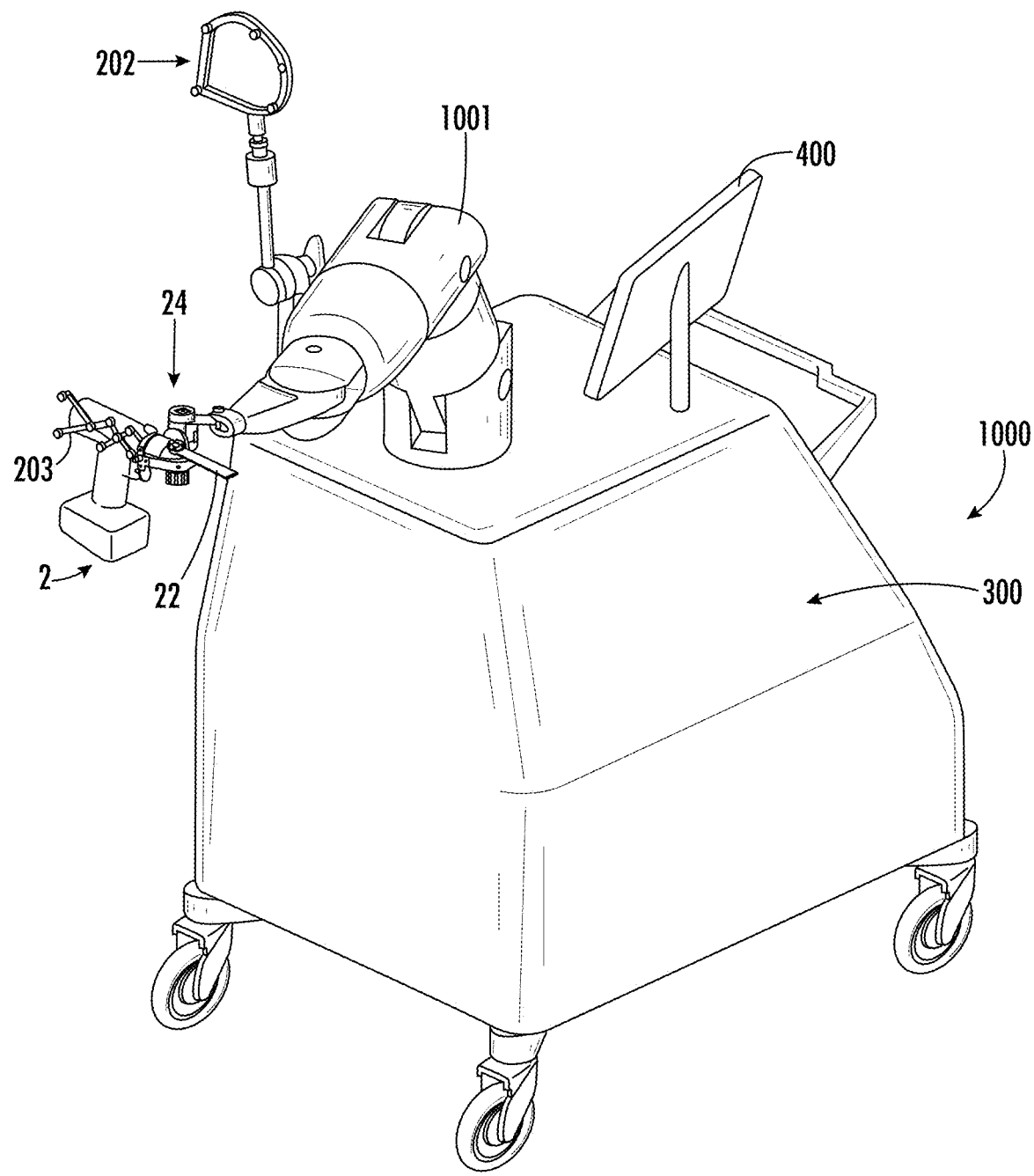
FIG. 18 illustrates a situation where a large robot with six degrees of freedom is equipped with a planar mechanism as used in the invention.

Incidentally, it is to be noted that the compensation method as described above is also advantageous for large surgical robots with six degrees of freedom holding a planar mechanism. Indeed, since the planar mechanism is very close to the surgical field, it has to remain compact and thus prone to bending under efforts exerted by the surgeon when cutting. Even if the large surgical robot is accurate, it cannot itself compensate for such bending of the planar mechanism. However, using a tracker on the cutting tool and implementing the above-mentioned compensation method allows overcoming this problem. FIG. 18 illustrates such a large robot. The robot 1000 comprises an arm 1001 having a serial architecture comprising six motorized degrees of freedom, a planar mechanism 24 connecting the last segment of the arm to a cutting tool 2. The robot is used with a tracking unit configured to determine in real time the pose of the cutting plane with respect to the coordinate system of the anatomical structure of the patient. The tracking unit comprises at least one tracker (not shown) configured to be attached to the anatomical structure, a tracker 202 attached to a segment of the arm of the robot and a tracker 203 attached to the cutting tool 2. The robot is controlled by a control unit configured to determine the pose of the cutting plane with respect to the target plane and to control the arm so as to bring the cutting plane into alignment with the target plane. The control unit is configured to implement a compensation method including the following steps:

(S'1) determining poses of the arm, the cutting tool and the anatomical structure using localization information provided by the trackers of the tracking unit;

(S'2) computing a deviation between the cutting plane and the target plane;

if the deviation is less than a threshold, allowing operation of the cutting tool and returning to step (S'1) to determine a new pose of the arm, cutting tool and anatomical structure;

if the deviation is greater than or equal to the threshold, projecting (S'3) the cutting plane and the target plane in the coordinate system of the robot, (S'4) computing a transformation between the plane of the planar mechanism and the cutting plane;

(S'5) updating the target plane with the transformation computed in step (S'4);

(S'6) computing a new attitude of the robot to reach the updated target plane, and determining the movements to be applied by the motors of the arm.

Advantageously, the attachment of the trackers to the cutting tool and/or actuation unit is reversible and reproducible.

According to an embodiment, instead of the tracker being attached to the actuation unit, the system also comprises a tracker attached to the intermediate part (part 7 shown in FIGS. 11-14) connecting the support unit to the holding arm or to the actuation unit, to the holding arm provided that the connection between the robotic device and the holding arm is sufficiently rigid (without any mechanical play), and/or a tracker attached to any other component rigidly connected to the robotic device.

As mentioned previously, a user interface is defined so as to show the user a potential position and orientation of the actuation unit suitable for aligning the cutting plane with a target plane.

From time to time, the user interface may provide information to the user to guide him or her to reposition the actuation unit in an optimal pose to enable alignment of the cutting plane with a target plane. The user interface may also indicate to the user if all targeted cutting planes can be reached from the current position of the actuation unit, and if not, in which direction to move to reach an optimal position.

Said user interface may be visual and/or acoustic.

According to an embodiment, the user interface may comprise a screen connected to the control unit, e.g. the screen 400 shown on FIG. 2.

Figure 19A:
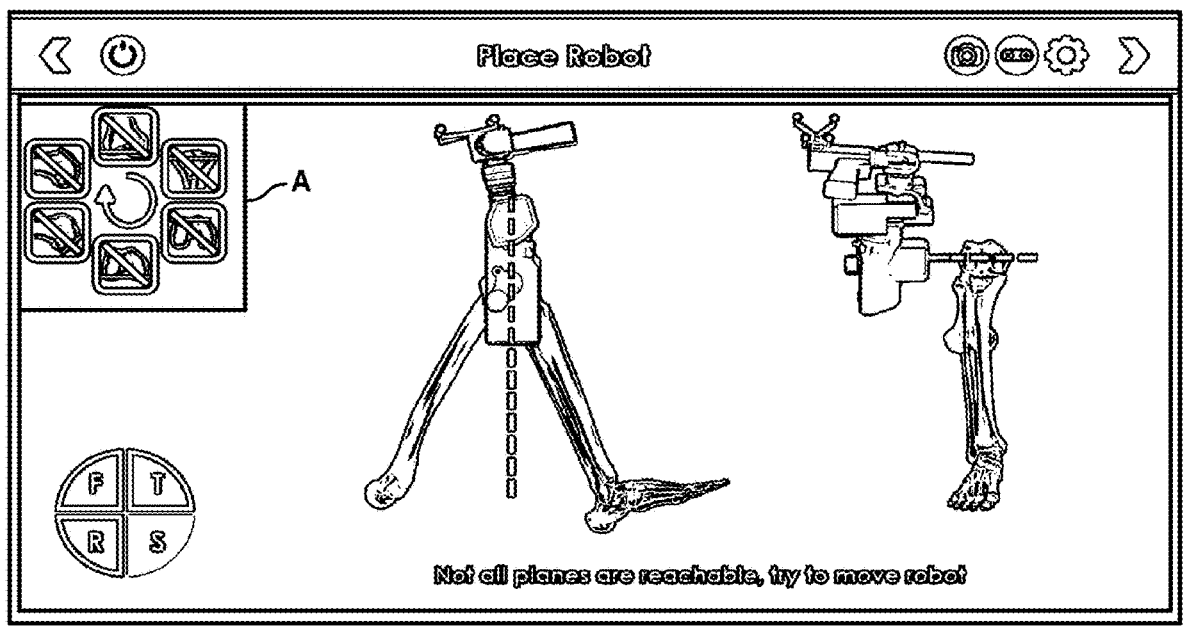
FIGS. 19A-19C illustrate an embodiment of the user interface for guiding the positioning of the robotic device to carry out several cuts on the femur and the tibia.
Figure 19B:
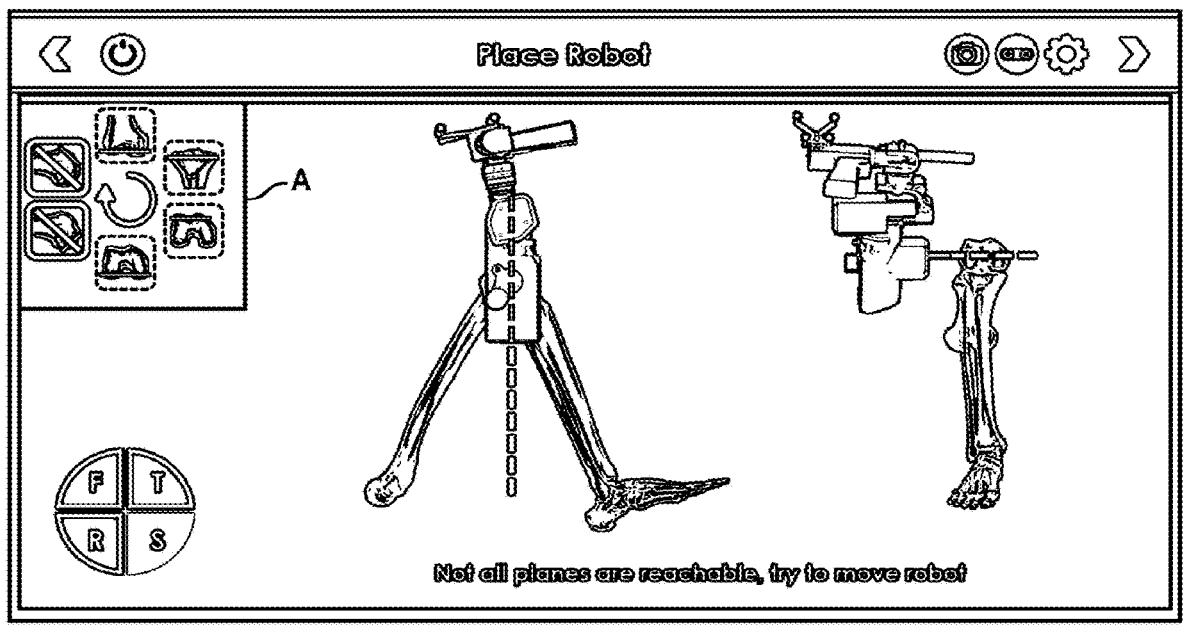
Figure 19C:
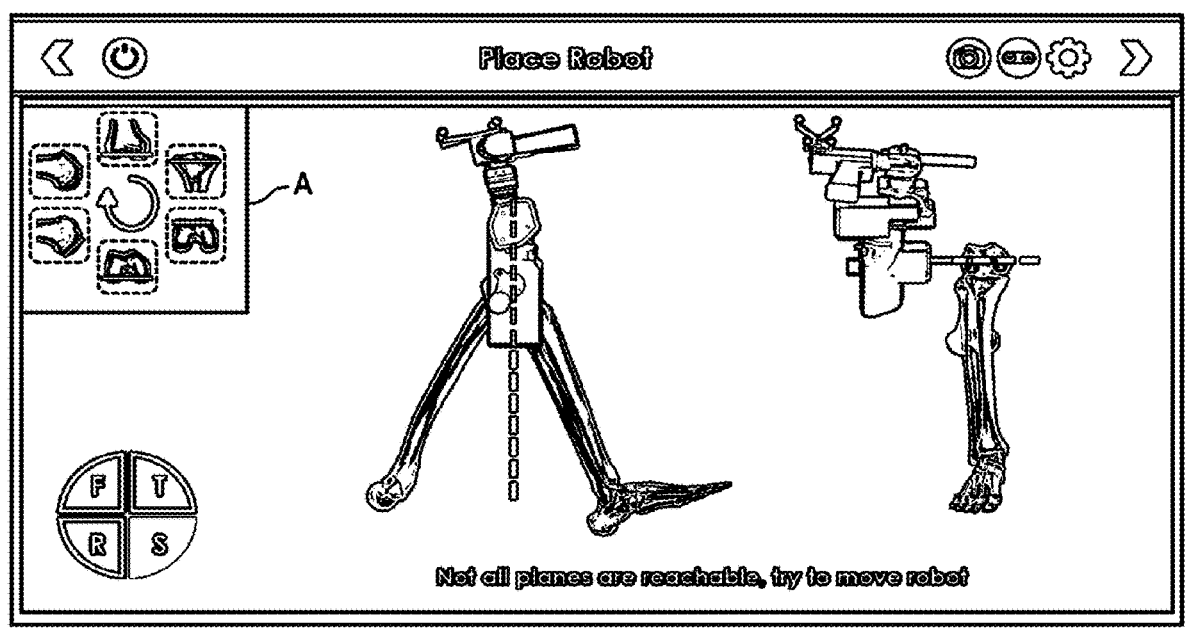

FIGS. 19A-19C show three views of the screening corresponding to different poses of the robotic device. In the situation of FIG. 19A, the robotic device is in a position and orientation that does not enable performing any of the planned cuts. This is illustrated by the icons in region A representing each of the six target planes required for TKA being crossed. In the situation of FIG. 19B, the robotic device is in a position and orientation that enables performing some of the planned cuts, but not all. This is illustrated by the icons representing two of the six target plans required for TKA being crossed in region A. In the situation of FIG. 19C, the robotic device is in a position and orientation that enables performing all of the planned cuts. This is illustrated by the fact that none of the icons of region A representing the six target planes required for TKA is crossed.

Thus, with such a user interface (other embodiments are described below), the user is able to position the robotic device so that the system is capable of performing all six cuts (five femoral cuts and one tibial cut) for TKA without requiring any repositioning of the robotic device. In this way, TKA surgery can be implemented much faster than with prior art devices.

If a realistic 3D model of the anatomical structure is available (i.e. obtained by pre-operative or per-operative imaging of the patient), it may be displayed on the screen, along with a real-time representation of the cutting tool (e.g. envelope of the oscillating blade). For instance, if the cutting tool is a saw, the user can visualize the position of the tip of the saw blade relative to the bone, to ensure that the tip of the saw blade does not exit from the bone. In case the planar mechanism connecting the saw to the actuation unit is motorized, this control may be automated.

During the use of the device the control system checks in real time if the saw can be aligned with a target plane. If the robotic device is moved such that the saw cannot be aligned with said target plane—e.g. in case of vibrations, and/or an involuntary movement of the patient—, then the information provided to the user may change, e.g. the color of the arrow is changed or an acoustical feedback is produced.

According to another embodiment (not shown), the user interface comprises visual indicators such as LEDs. These LEDs may be arranged on a supporting surface that is fixed to the robotic device. Alternatively, the LEDs may be arranged on a support separate from the robotic device and connected to it by a wire. Alternatively, the LEDs may be arranged on a support separate from the robotic device and wirelessly linked to the robotic device. Such a separate support can be placed in the vicinity of the robotic device/cutting tool, in the user's field of view.

Said indicators are intended to instruct the user not to activate the cutting tool, in case the robotic device is not able to compensate for a misalignment between the cutting plane and the target plane. For example, a red and blinking light is turned on as soon as the trackers mounted on the anatomical structure and/or the cutting tool are not visible. It is turned off or changed to a green light as soon as the visibility of trackers is restored.

Another way of providing information to the user is to use numerical displays (e.g. provided by LCD screens) that represent virtual spirit levels. The general orientation of the robotic device can be adjusted by the user based on one virtual spirit level on top of the robotic device and another one on a side (opposite to the patient's leg) of the robotic device. The distance of the robotic device can be adjusted using a support unit, and/or using indicators such as LEDs representing an arrow pointing the desired direction, and/or via the screen of the user interface.

The system further comprises a control unit which is intended to control the pose of the saw in an optimal way in order to align it with a target plane.

According to an embodiment, the control unit may be coupled to the surgical saw used to perform the cut and configured to allow the actuation of the saw only when the cutting plane is aligned with the target plane. This increases the safety of the system.

FIG. 20 shows an embodiment of a setup of the robotic device illustrated in FIGS. 3-3B.

The patient (only one flexed leg is represented in FIG. 20) is lying on an operating table 500, with the lower leg supported by a leg holder 600. A tracker 201 is fixed to the femur and another tracker 201 is fixed to the tibia.

The holding arm 5 has one end attached to the leg holder 600 and the opposite end attached to the actuation unit 4.

The holding arm can be freely manipulated by the user so as to bring the robotic device in the desired position relative to the patient, and bears the weight of the robot. The arm 5 can be locked once the desired position has been achieved. The holding arm may be one of the arms described with reference to FIGS. 9 and 10.

In this setup, the robotic device does not comprise any support unit. However, a support unit could be provided (in addition to the holding arm) without departing from the scope of the invention.

A tracker 202 is fixed to the second segment of the actuation unit 4 of the robotic device.

The saw 2 is connected to the third segment by a passive planar mechanism 24.

A tracker 203 is also attached to the saw 2, which allows compensating mechanical play that may exist between the robotic device and the saw.

Figure 21:
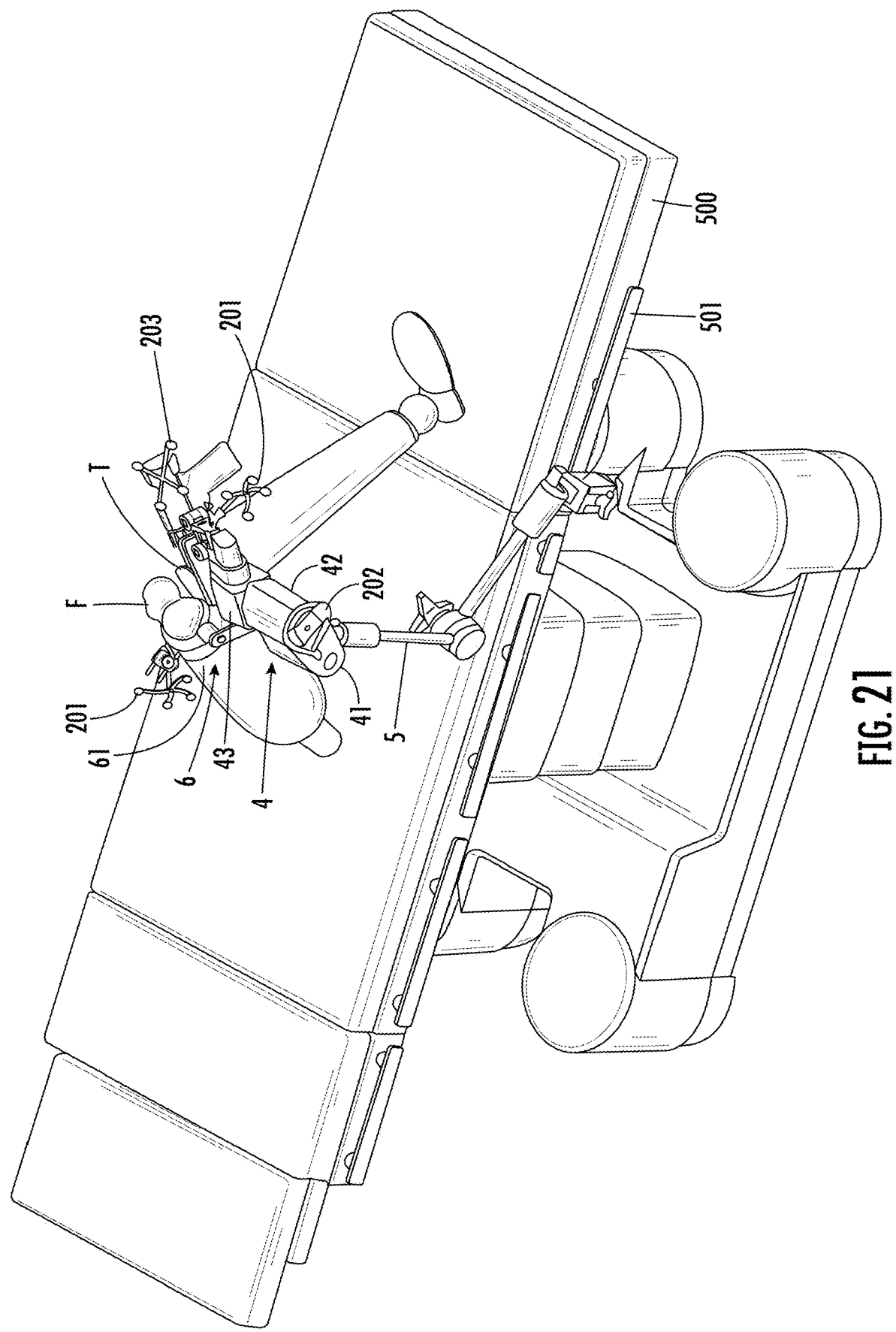
FIG. 21 shows a setup of the robotic device according to another embodiment.

FIG. 21 shows another embodiment of a setup of the robotic device illustrated in FIGS. 3A-3B.

The patient (only one leg is represented in FIG. 21) is lying on an operating table 500, with the leg in flexed position. Although not illustrated, the patient's leg can be maintained in said flexed position by wedges commonly used in surgical interventions. For example, one wedge can be placed under the foot and another one can be placed on the external side of the hip, in order to reduce inward and outward movements of the flexed leg.

A tracker 201 is fixed to the femur and another tracker 201 is fixed to the tibia.

The holding arm 5 has one end attached to a rail 501 arranged on the operating table 500 and the opposite end attached to the actuation unit 4. The rail to which the holding arm is attached may be the rail located on the same side of the table as the leg of interest, or the rail located on the side of the table opposite to the leg of interest.

The actuation unit is also attached to a strap 61 arranged around the upper leg, which provides a support unit 6 creating a partial mechanical link between the anatomical structure and the actuation unit 4. Due to the fact that the support unit makes either direct contact with the anatomical structure to be cut or indirect contact via a region of the patient's body adjacent to the anatomical structure to be cut (here, the soft tissues surrounding the femur), the support unit has the effect of a partial mechanical link that limits the movements of the user when operating the device—and, in advantageous embodiments, also damps movements of the user and/or the patient, vibrations of the cutting tool and reaction forces caused by movements of the actuation unit.

A tracker 202 is fixed to the second segment of the actuation unit 4 of the robotic device.

The saw 2 is connected to the third segment of the actuation unit 4 by a passive planar mechanism 24.

A tracker 203 is also attached to the saw 2, which allows compensating mechanical play that may exist between the robotic device and the saw.

Figure 22:
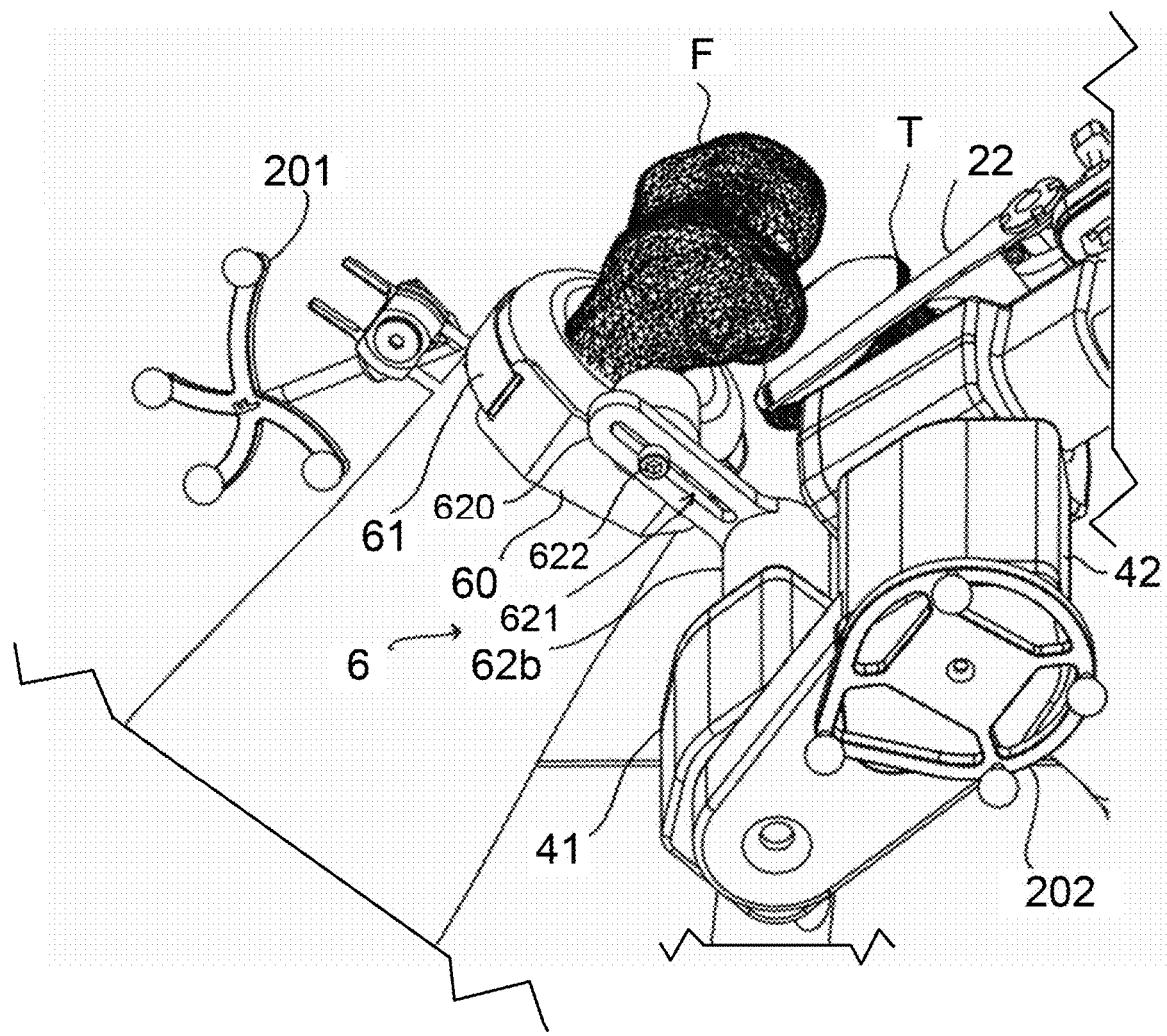
FIG. 22 shows a setup of the robotic device according to another embodiment.

FIG. 22 shows another embodiment of a setup of the robotic device illustrated in FIGS. 3A-3B.

The patient (only one flexed leg is represented in FIG. 22) is lying on an operating table 500, with the lower leg supported by a leg holder 600. A tracker 201 is fixed to the femur and another tracker 201 is fixed to the tibia.

The holding arm 5 has one end attached to the leg holder 600 and the opposite end attached to the actuation unit.

As in the embodiment of FIG. 21, the actuation unit 4 is also attached to a strap arranged around the upper leg, which provides a support unit 6 creating a partial mechanical link between the anatomical structure and the actuation unit.

Figure 23:
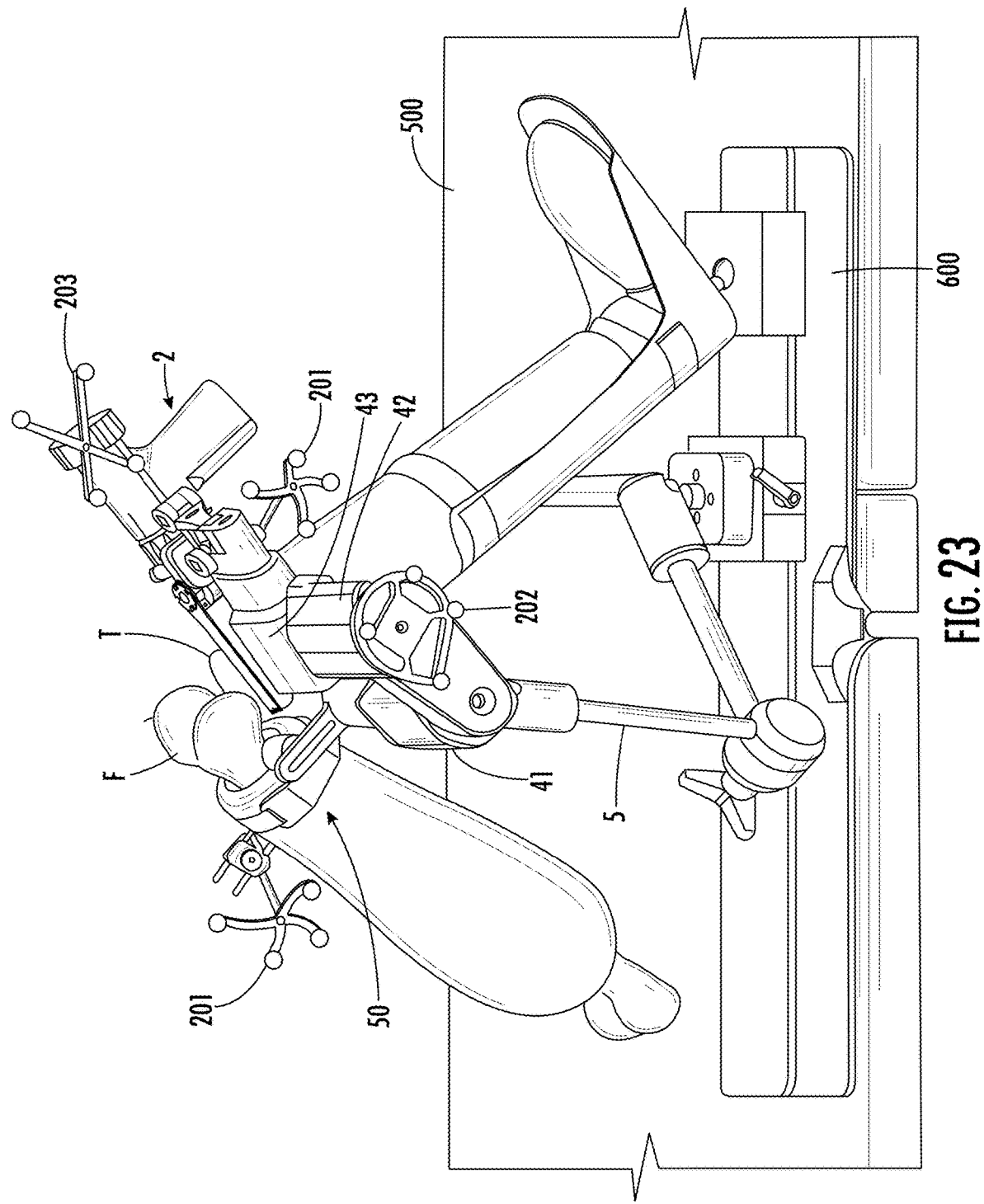
FIG. 23 is an enlarged view of FIG. 21 or 22, showing an embodiment of the support unit.

FIG. 23 is an enlarged view of FIG. 21 or 22 to better show the support unit.

The support unit 6 comprises a flexible strap 61 and a rigid support 60 that together enwrap the soft tissues around the patient's femur F. The flexible strap 61 allows tightening the rigid support 60 to the leg, the tension of the flexible strap being adjusted depending on the diameter of the patient's leg. Cushions of different thicknesses can be inserted between the rigid support and the patient's skin to adapt to various sizes of the leg. It is also possible to use a spring mechanism to exert a pressure on the side of the rigid support, which provides a variable adjustment to individual patients. Finally, a mechanical system 62 enabling to take away the rigid support 60 of the support unit from the actuation unit 4 can be used. The distance can be set by the means of discrete positions or by a clamping mechanism.

In any embodiment, the support unit attached to the thigh can be used for performing the cuts on the tibia bone since the tibia and femur are linked by soft tissues creating a mechanical link that stabilizes the motions. In another embodiment, the support unit can be attached to the lower part of the leg (tibia) and the actuation unit is used to perform all cuts on the femur and tibia bone.

A base 62b of the support unit is attached to the first segment 41 of the actuation unit 4 (which is also rigidly attached to the holding arm), so as to freely rotate around the first axis.

The base 62b comprises a radially extending member 620 provided with a central groove 621.

The base 62b is connected to the strap support 622 by a screw slidably engaging the central groove 621. The distance between the actuation unit and the leg can be adjusted by moving the base 62b relative to the screw 622. Once the desired distance has been obtained, the screw 622 is tightened so as to rigidly connect the base to the strap support 60. According to other embodiments illustrated in FIGS. 11-12, it is also possible to use a radially extending member without such a screw and groove for adjustment, providing a fixed distance between the actuation unit and the leg, and only connected to the actuation unit, the holding arm or the intermediate part by a pivot link. It is also possible to eliminate the movements and adjustments of the support unit using a fixed element relative to the base of the actuation unit.

FIG. 23 shows only one example of the support unit and the skilled person may design the support unit to include a greater number of settings (translational and/or rotational) to adjust the position of the robotic device relative to the leg.

Although the support unit is represented around the femur in FIGS. 21, 22 and 23, it could be attached to the tibia, or to both the femur and the tibia.

Figure 24A:
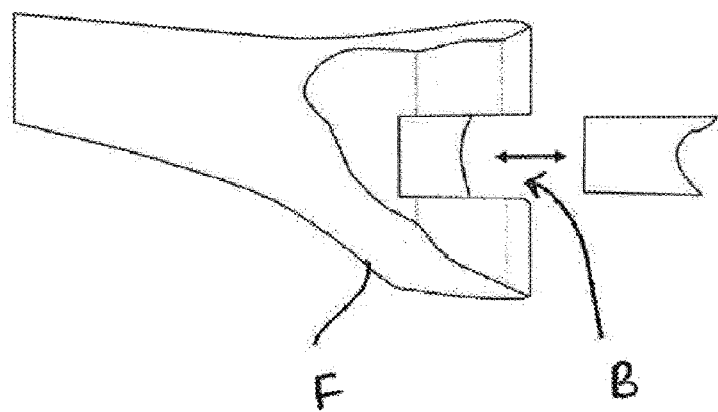
FIGS. 24A-24C illustrate an application of the robotic device to perform vertical cuts.
Figure 24B:
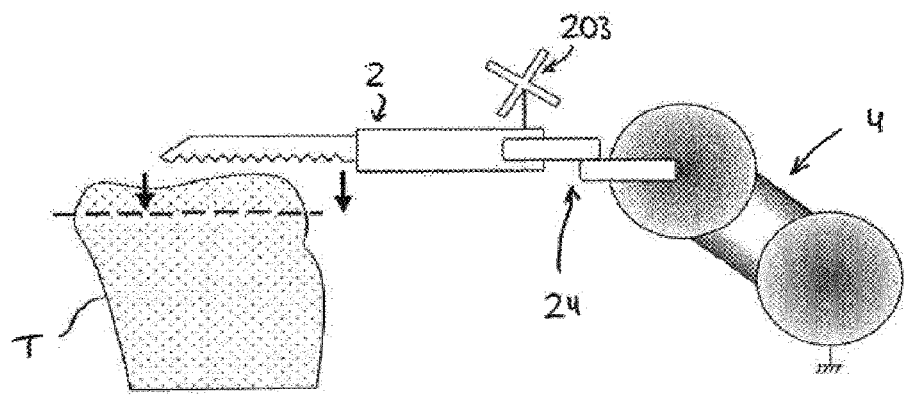
Figure 24C:
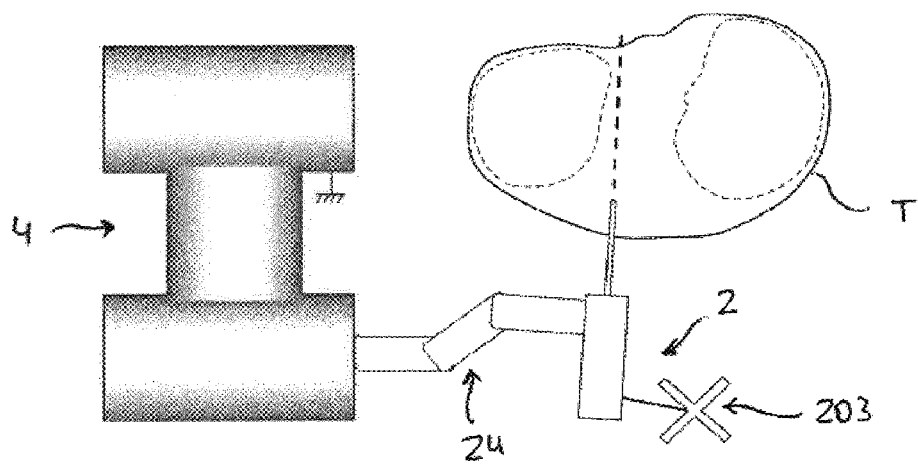

FIGS. 24A to 24C illustrate another application of the robotic device. In this embodiment, the cutting tool is a reciprocating saw orthogonal to the plane of the planar mechanism.

This saw may be used to perform so-called vertical or sagittal cuts. In particular, during a TKA surgery, these vertical cuts allow forming in the femur a box B configured to receive a postero-stabilized (PS) femoral component (see FIG. 24A). During UKA surgery, the reciprocating saw can be used to perform the sagittal cut necessary to install the tibial implant.

Before starting the cut, the first step is to align the planar mechanism 24 with a plane orthogonal to the cut (e.g. the sagittal cut on the tibia, see FIG. 24B). The actuation unit 4 constrains the planar mechanism 24 inside a given plane above or below the bone material to be cut.

If the planar mechanism is active (fully motorized), the saw can then be positioned by the system automatically/actively.

Otherwise, if the planar mechanism is partially active (with a combination of motorized and non-motorized degrees of freedom) or fully passive, the saw 2 must be localized in 3D thanks to a tracker 203. An interface showing the saw position and orientation relative to the bone and to the target plane is displayed to assist the surgeon. Then the surgeon can move the saw 2 until it reaches a target position and orientation (which is a line (hereinafter called "target line", represented by a dotted line) when considered in the plane orthogonal to the target plane) (see FIG. 24C).

Another option, if the planar mechanism is partially or fully active, or equipped with a position locking mechanism, is to let the surgeon displace the reciprocating saw to the right position, and then lock or constrain the saw blade to remain inside the target line once it has been reached.

Then, the cut can be performed, moving the reciprocating saw up or down.

According to a first option, the actuation unit displaces the saw actively, by regularly changing the planar mechanism plane (lowering or raising it). The cutting action of the saw must be enabled during this process so that the cut can be realized while the actuation unit actually moves. In a preferred embodiment, the cutting action of the saw is switched on or off by the control unit of the system. If the planar mechanism is not fully active, the surgeon may have to maintain the saw blade in the right orientation during the cut. At any time, if the planar mechanism orientation or position deviates from the target line more than a predetermined threshold (e.g. 2 degrees or 2 mm), the actuation unit will stop lowering or raising the planar mechanism plane. Additionally, for the sake of safety, the displacement of the planar mechanism plane should only be possible if the surgeon maintains the cutting action enabled, e.g. using a foot switch and/or a trigger pressed. As soon as the foot switch or trigger is released, the actuation unit will stop lowering or raising the planar mechanism plane. Optionally, the speed of displacement of the planar mechanism plane may be modified during the cut based on its level of advancement. For instance: the speed may be low at the beginning to avoid slipping or other causes of a loss of alignment due to the initial contact between the saw blade and the bone surface; then the actuation unit can move faster in the middle of the cut; and eventually it can progressively slow down to zero until the cutting limit (e.g. the tibial cut plane) is reached, with various predefined speed profiles.

According to another option, the surgeon pushes up or down on the saw to perform the cut. The robotic device detects the direction and strength of the force applied by the surgeon and the actuation unit shifts the planar mechanism plane accordingly (maintaining its orientation so that it always remains orthogonal to the target plane). If the blade reaches a limit (for instance the planned or already performed transverse tibial cut in case of UKA), then the actuation unit does not move anymore, preventing the saw from being lowered or raised anymore, so that the surgeon feels that the limit has been reached. In the same spirit as the previous section, the counter-force applied by the actuation unit may vary depending on the level of advancement of the cutting process.

By default, it is assumed in the above description that the reciprocating saw is rigidly fastened to the planar mechanism. However, it would be possible to only use a partial mechanical link (for instance the saw could even only rest on the planar mechanism, maybe with a simple interface with complementary features to prevent unwanted translation between the saw and the planar mechanism). This way the planar mechanism will mainly serve as a guard to prevent the saw from cutting too low or too high. It can also partially guide the saw as it is displaced orthogonally to the sagittal cut. Moreover, to prevent wrong cuts, the actuation unit may move only if the saw position and orientation is maintained within a predefined range (e.g. 2 mm and 2 degrees) relatively to the target line.

Figure 25:
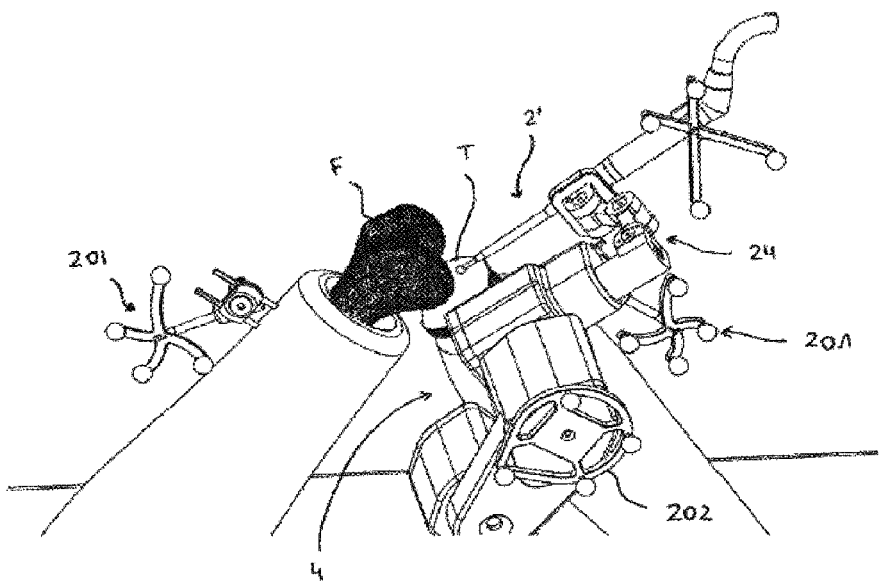
FIG. 25 illustrates an embodiment of the robotic device wherein the cutting tool is a burr.

FIG. 25 illustrates a setup of the robotic device illustrated in FIGS. 3A-3B, with a burr 2' as the cutting tool.

Although the trackers illustrated in the figures are optical trackers, it should be noted that any other tracking technology (e.g. electromagnetic) may be used.

It should be noted that the embodiments described above may be combined.

In addition, the holding arm—and, if any, the support unit which only provides a partial mechanical link—does not require any invasive action onto the patient while fully supporting the weight of the robotic device.

Thus, as compared to the large screws and pins that are implanted in the bone (i.e. that penetrate the bone on several centimeters) in document US 2011/0130761, the robotic device according to the invention is not fixed directly to the patient but held by the holding arm which is attached to a component (operating table, leg holder . . . ) non-invasively fixed to the patient, and may only be coupled directly to the patient by non-invasive attachment means (e.g. a strap, etc.).

Micro or macro motions of the robotic device with respect to the anatomical structure to be cut, including slow and fast motions, are compensated within a tolerance range and a given time frame that defines the precision of the device.

Typically, for bone surgery applications, motions in the range of a few tenths of a millimeter need to be compensated to obtain sufficient precision; such a compensation requires ultrafast motion detection and measurement, as well as calculation of the compensation motion to be applied and execution of the desired compensation motion.

Large surgical robots with six degrees of freedom are very stiff but are very cumbersome and expensive; besides, they have a considerable inertia (especially on the first mobile segment), which is not compatible with real time control of the cutting plane. On the other hand, existing small, lightweight robots cannot be used if they are not rigidly attached to the anatomical structure. By contrast, the invention provides a compact, lightweight robotic device that allows real time control of the cutting plane without requiring any invasive fixation to the patient.

Figure 27:
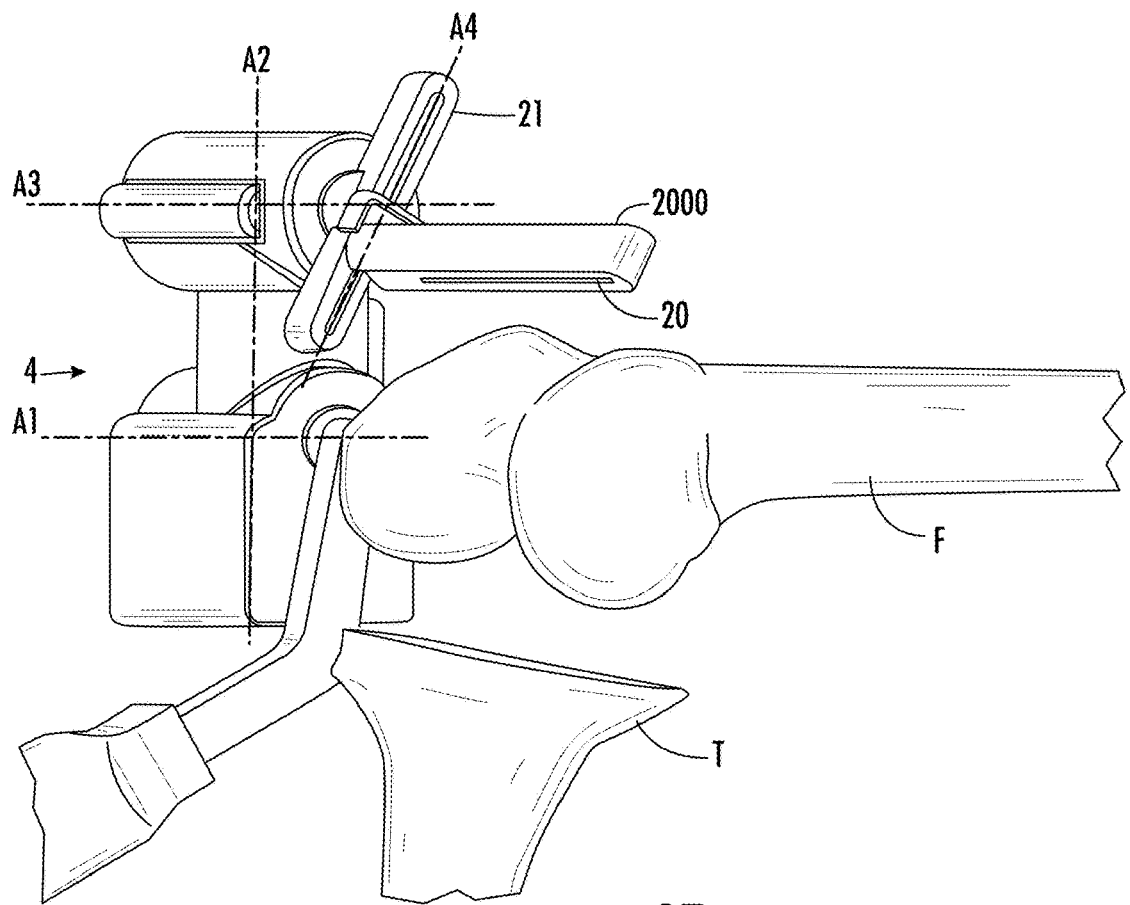
FIG. 27 shows an embodiment of the device wherein the cutting block is mounted on a slider intended to adjust the distance between the cutting block and the bone to be cut.

Although the previous description has been made with reference to a cutting tool that is attached to the actuation unit via the planar mechanism, embodiments comprise a cutting block attached to the actuation unit via the planar mechanism described above or via a slider (see FIG. 27). The cutting block comprises at least one slot that defines a guiding plane which corresponds to the cutting plane of the cutting tool. Each slot allows constraining a cutting tool held in a users hand in the respective guiding plane. This cutting tool can be a sagittal saw, a reciprocating saw, or even a burr as described above.

Figure 28A:
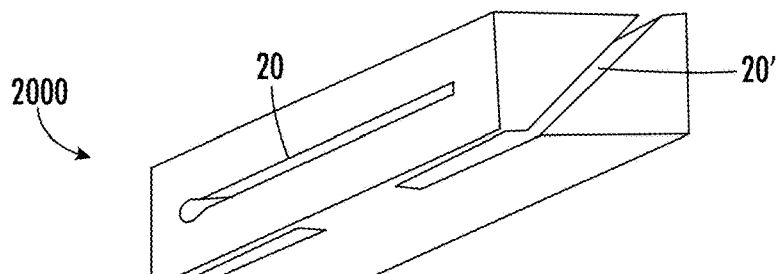
FIGS. 28A-28B show perspective views of a cutting block comprising respectively two and three slots for insertion of a cutting tool.
Figure 28B:
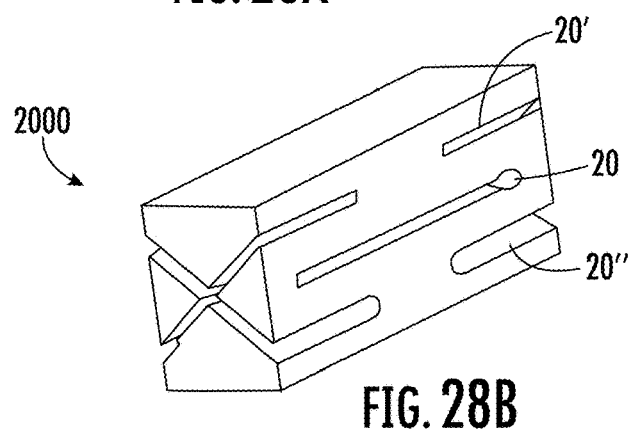
Figure 29A:
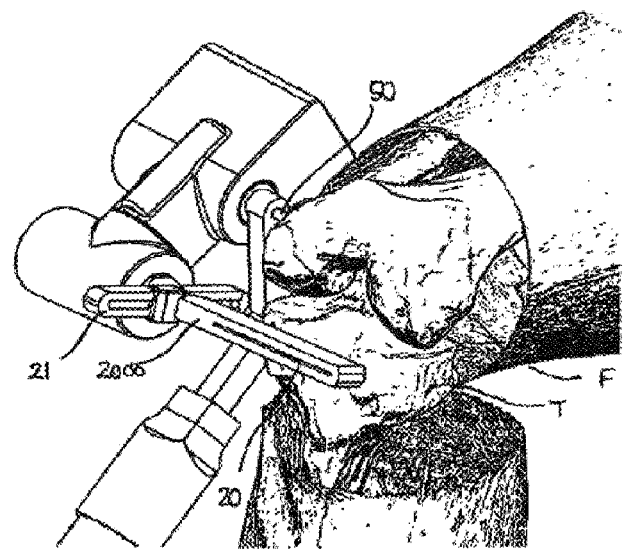
FIGS. 29A-29F show perspective views of the robotic device with the cutting block positioned to cut the tibia and to carry out the femur distal cut, the anterior cut, the posterior cut, the anterior chamfer and the posterior chamfer cuts, respectively.
Figure 29B:
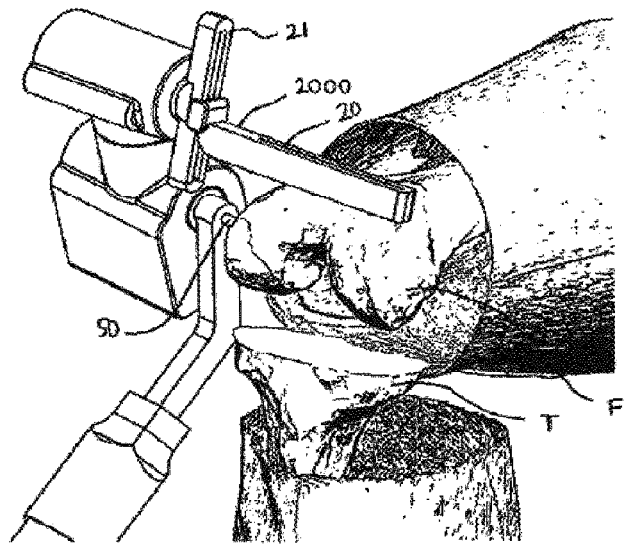
Figure 29C:
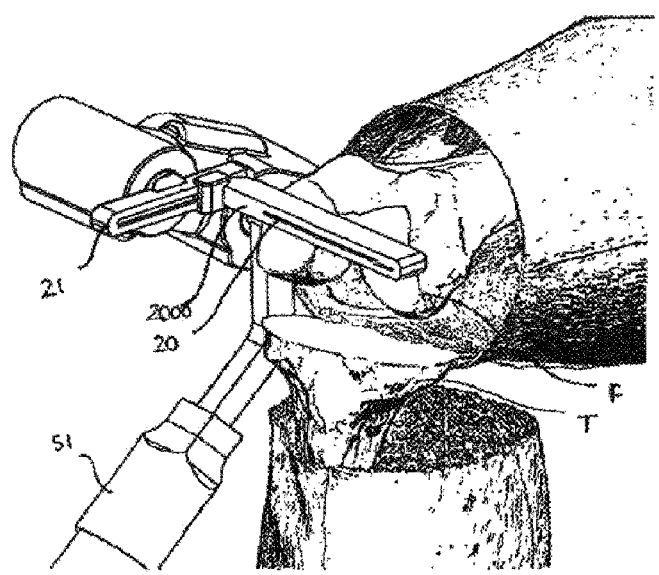
Figure 29D:
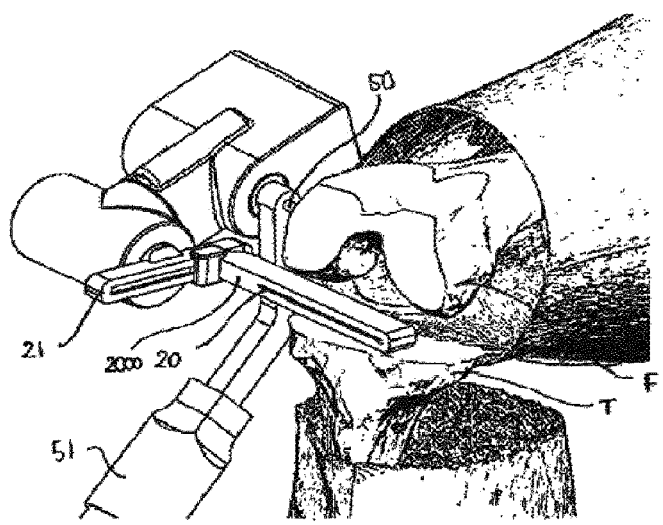
Figure 29E:
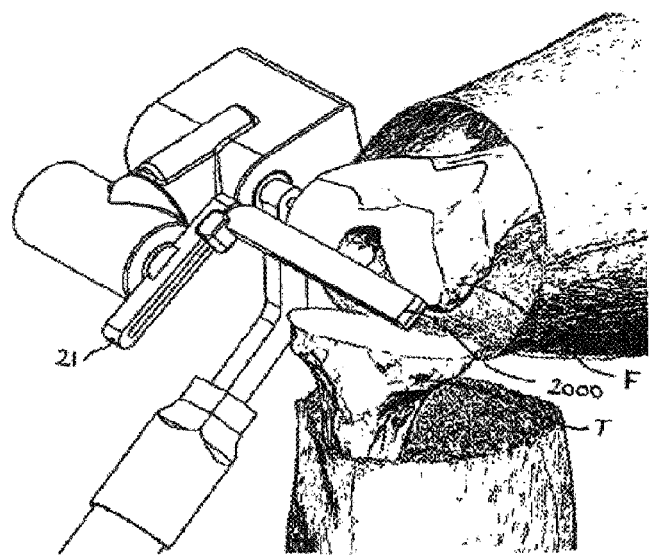
Figure 29F:
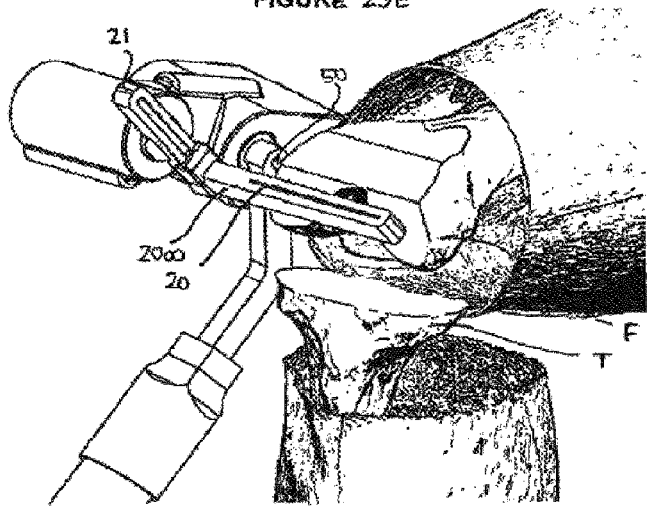

According to particular embodiments, the cutting block 2000 may comprise two slots 20, 20' (see FIG. 28A) or three slots 20, 20', 20" (see FIG. 28B). Thus, once the cutting block has been positioned with one slot in alignment with a target plane, only a slight adjustment of the pose of the cutting block is necessary to align another slot with another target plane. The slots may even be arranged in a given relative position such that, once one slot has been placed in alignment with a target plane, at least one other slot is also aligned with another target plane. In this way, it is possible to carry out several cuts without moving the cutting block and the robotic device.

In order to provide an optimal guidance of the saw blade and avoid any deviation of the saw blade, the width w of the slot is as large as possible. For example but not limited to, the width of the slot may range from 10 to 25 mm.

Figure 30:
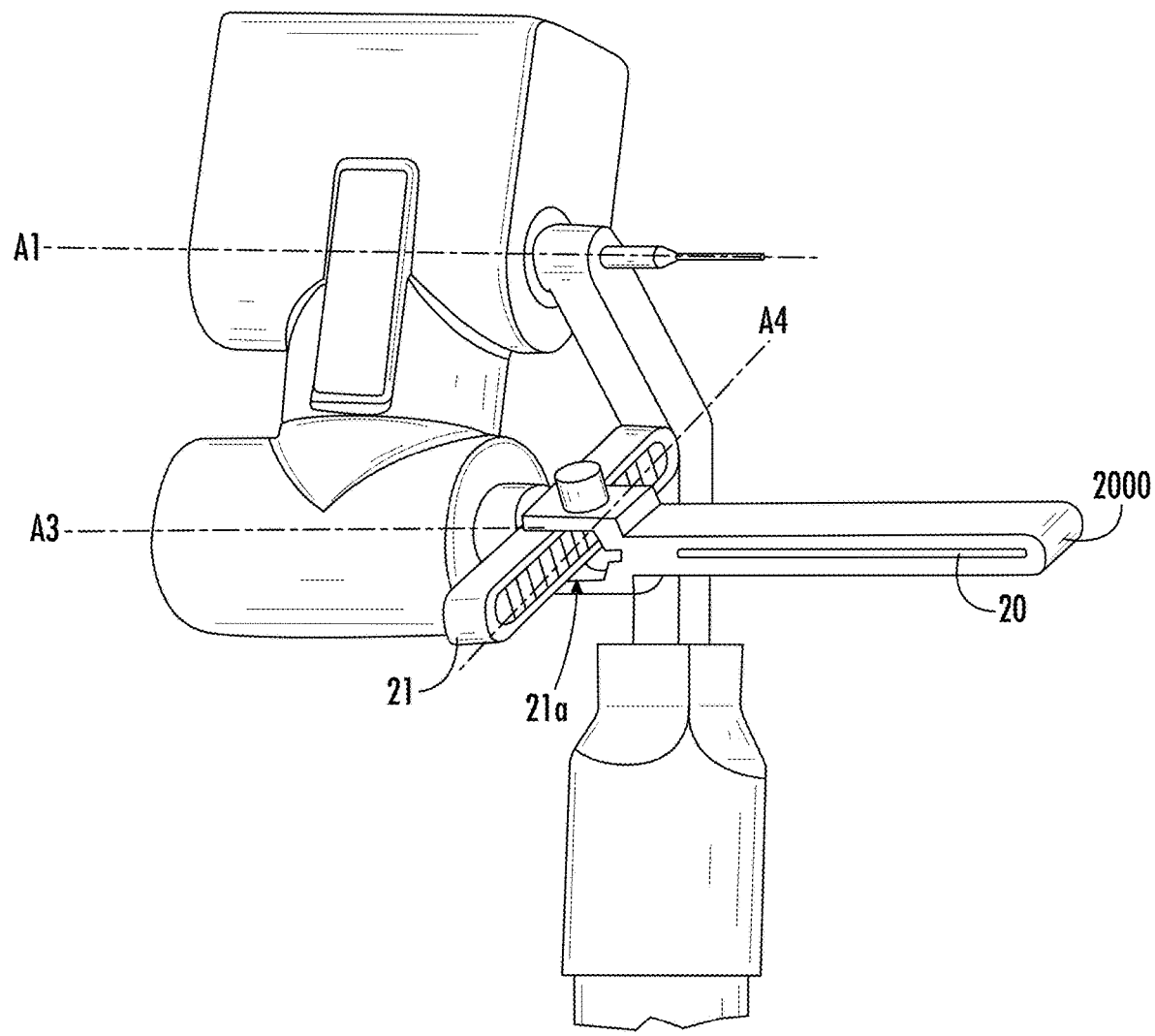
FIG. 30 shows an embodiment of the device wherein the slider onto which the cutting block is mounted comprises a plurality of determined positions provided by a rack and pinion mechanism.

The planar mechanism or the slider provides an additional degree of freedom in translation along an axis A4 which is parallel to the plane defined by the slot 20 (see FIGS. 29A-29F and 27). Such a slider allows maintaining the distance between the rotation axes of the actuation unit to a small distance, the additional translation along the slider providing access of the cutting block to farther regions of the anatomical structure. According to an embodiment, the slider is manually operated. As shown in FIG. 30, the slider may be provided with a rack and pinion mechanism 210 in order to provide a plurality of determined positions. According to an embodiment, the slider may be biased by an elastic member such as a spring (not shown). According to an embodiment, the slider may be motorized, thus providing a fourth motorized degree of freedom controlled by the control unit, within the target plane. Once the position of the cutting block has been adjusted, the slider may be blocked to avoid any further movement of the cutting block.

The planar mechanism may further allow pivoting the cutting block around a fifth axis A5 which is substantially orthogonal to the plane defined by the slot 20. This enables placing the cutting block closer to the bone without changing the orientation of the guiding plane. This rotational degree of freedom of the cutting block can also be combined with the translational degree of freedom provided by the above-mentioned slider.

In some embodiments, the support unit may be arranged between the cutting block and the patient.

For example, as shown in FIG. 31A, the cutting block 2000 comprises at least one flexible interface (e.g. one or more silicone cushions 56) configured to contact the anatomical structure. In this way, the cutting block may be pressed against the anatomical structure (e.g. using a slider as described above), thus ensuring a partial mechanical link. The pressure can be applied against the holding arm 5 in combination with a leg holder that holds the knee substantially still. However, it is still possible to slide by a few degrees or millimeters the flexible interface along the anatomical structure to adjust its position. In this embodiment, the actuation unit is connected to the anatomical structure via the cutting block 2000 and the support unit is made of the silicone cushion(s) 56. According to a preferred embodiment, the flexible interface comprises two silicone cushions disposed on both sides of the slot 20 of the cutting block, with a sufficient distance between both cushions so as to avoid damaging them when cutting with the saw. Instead of silicone, any soft biocompatible material can be used.

According to another embodiment (not shown), the cutting block may comprise an interface made of a plurality of sharp teeth. In this way, the cutting block may be pressed and retained against the anatomical structure by the teeth, thus ensuring a partial mechanical link.

According to another embodiment, the cutting block may be fixed to the anatomical structure by small pins 57 (see FIG. 31B). Said pins can be drilled and removed automatically using dedicated motors controlled by the control unit.

The tracking unit may comprise a tracker attached to the cutting block or to the cutting tool.

Such a cutting block may in particular enable cutting the lateral walls of a box within the anatomical structure in order to create a notch. This is necessary to position femoral implants that are postero-stabilized and include a box in their design which necessitates to create a notch in the bone for perfect fitting.

Figure 32:
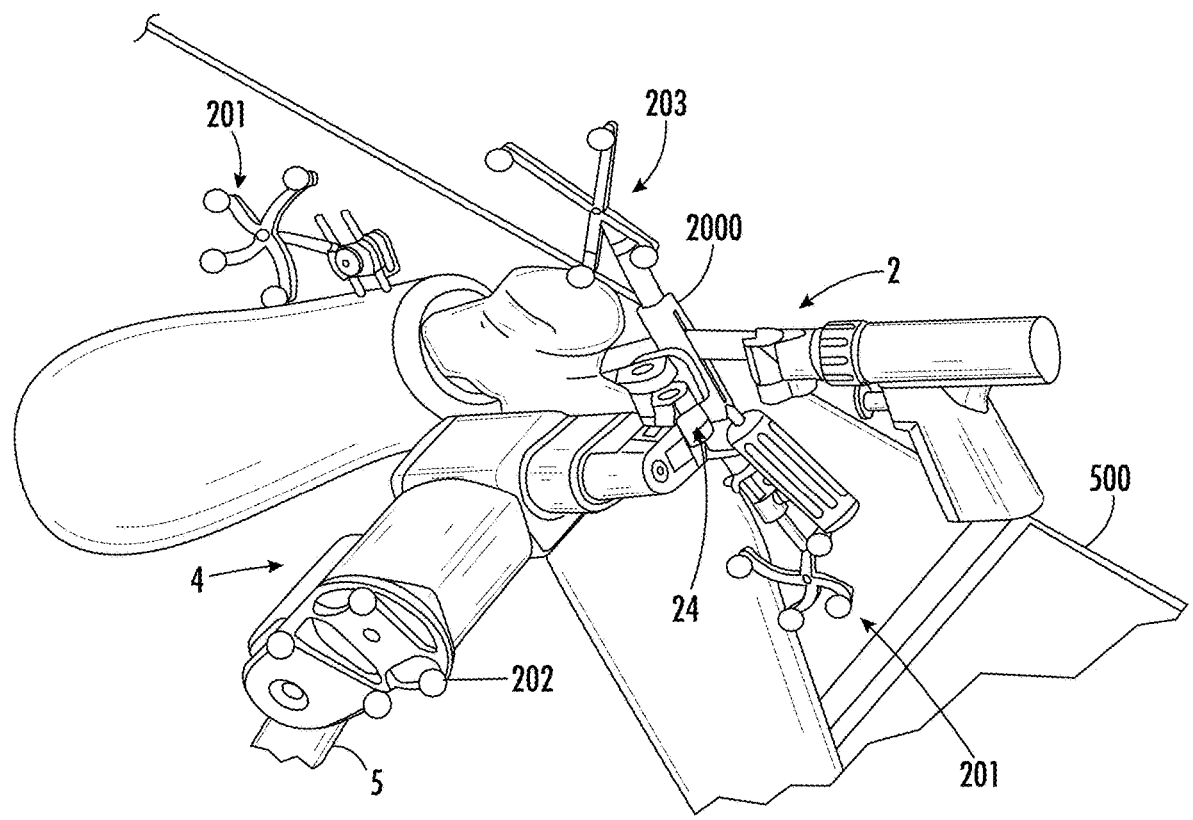
FIG. 32 illustrates a setup of the robotic device with a cutting block.

FIG. 32 illustrates a setup of the robotic device in such a situation.

The patient (only one flexed leg is represented in FIG. 32) is lying on an operating table 500. A tracker 201 is fixed to the femur and another tracker 201 is fixed to the tibia.

The holding arm 5 has one end attached to the table and the opposite end attached to the actuation unit.

In this setup, the robotic device does not comprise any support unit. However, a support unit could be provided, in addition to the holding arm 5.

A tracker 202 is fixed to the second segment of the actuation unit of the robotic device.

The cutting block 2000 is connected to the third segment of the actuation unit 4 by a passive planar mechanism 24.

A tracker 203 is also attached to the cutting block, which allows compensating mechanical play that may exist between the robotic device and the cutting block.

The cutting tool is a reciprocating saw 2 whose blade passes through the slot of the cutting block 2000.

Operation of the control unit will be described in more detail below.

Figure 33:
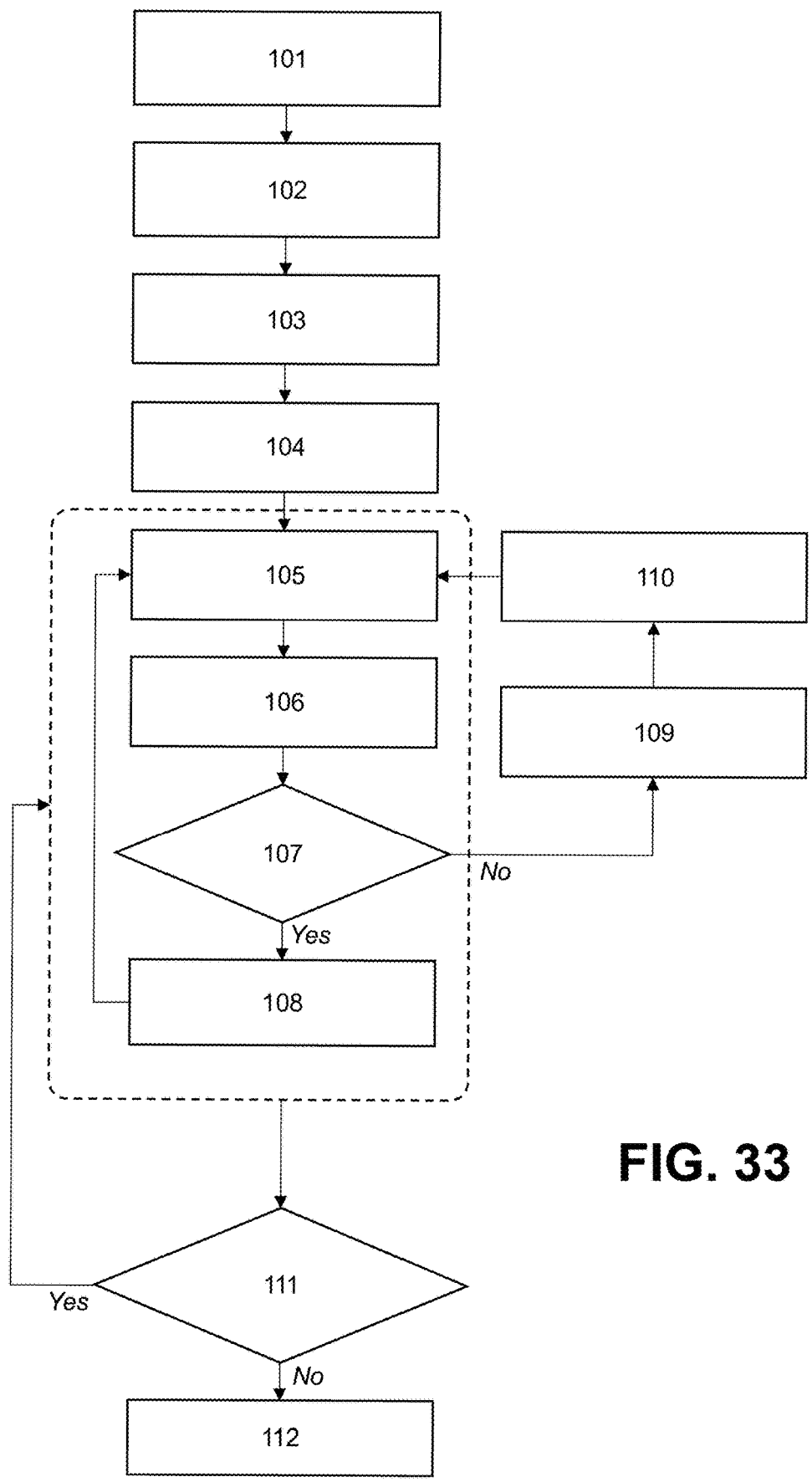
FIG. 33 is a flowchart of a surgical procedure for performing at least one osteotomy implementing an embodiment of the invention.

FIG. 33 is a flowchart of a complete surgical intervention intended to implement at least one osteotomy, such as total knee arthroplasty. It is to be noted that the initial and final steps may not form part of the invention.

In step 101, the patient's anatomy in the region to be treated by the surgical intervention is acquired. Said acquisition may be made, in a manner known per se, for example using imaging means for acquiring an image of the bones and/or a localized pointer (digitization probe) for acquiring a plurality of points of the bone surfaces as it is commonly used in image-free surgical navigation techniques.

In step 102, a surgical planning is carried out based on the acquired patient's anatomy. This planning step results in the definition of the pose of target planes intended to carry out the cuts.

In step 103, a user positions the robotic device with the holding arm in a rough position intended to allow performing the cuts according to the target planes. In this step, the patient's anatomy is also equipped with at least one tracker. The robotic device is also equipped with at least one tracker, so as to enable localizing the relative positions of the robotic device and anatomical structure to be cut. In this step, especially if several cuts are to be made without repositioning the robotic device, the user may use the user interface to determine a suitable position and orientation of the robotic device.

In step 104, the order of the cuts to be carried out is selected. To that end, the control unit retrieves the pose of the corresponding target plane. If several cuts are to be performed, they may be memorized in the system in a specific order, and loaded one after the other. Otherwise, the user interface may allow the user to select a specific cut. It is to be noted that this step may be carried out at any time before step 105.

In step 105, the control unit receives the tracking data of the trackers. Thus, the control unit is able to compute the current position of the robotic device relative to the anatomical structure to be cut.

Based on the current position of the robotic device, the pose of the target plane and the kinematic design of the robotic device, the control computes in step 106 a movement of the actuation unit allowing reaching the target plane. In step 107, the control unit checks whether the target plane is reachable by the robotic device in its current position (i.e. without moving the support unit). If so, the control unit commands the actuation unit to move the cutting tool or the cutting guide to the required position so as to have the cutting plane in alignment with the target plane (step 108).

If the current position of the robotic device does not allow achieving alignment on the target plane, the control unit warns the user that he cannot and must not perform the cut (step 109) and computes in step 110 a new position of the robotic device to reach the target plane (said new position implying moving the holder unit), and steps 105 to 107 are carried out again.

In step 108, once the cutting plane has been aligned with the target plane, the cut is allowed by the control unit (e.g. by providing an indication to the user that the cutting plane is aligned with the target plane, and/or by allowing the start of actuation of the cutting tool by the user). The user can perform the cut by operating a cutting tool within the cutting plane. During this cutting step, the control unit uses the tracking data to check whether the cutting plane remains aligned with the target plane (see the loop between steps 105 and 108).

Once the cut has been completed (after step 108), the user indicates to the control unit that the cut is finished. Said indication can be made for example by pressing a footswitch or a button.

In step 111, the user or the control unit checks whether there remain any cuts to be carried out.

If not, postoperative checks may be carried out in step 112.

If cuts remain to be carried out, steps 105-108 (and, if appropriate, 109 and 110) are iterated until all the planned cuts have been carried out.

The invention claimed is:
1. A surgical system, comprising:
a cutting tool having an attached tracker;
a planar mechanism having a first end connected to the cutting tool;
an actuation unit connected to a second end of the planar mechanism, the actuation unit for adjusting a position and orientation of the cutting tool, wherein the actuation unit has a serial architecture and at least three motorized degrees of freedom;
a passive articulated lockable holding arm connected to the actuation unit; and
a control unit configured to:
determine a pose of the cutting tool using data from sensing of the tracker;
determine a cutting plane based on the pose of the cutting tool;
detect whether the cutting plane can be aligned with a target plane for an anatomical structure of a patient, wherein the cutting plane is orthogonal to a plane defined by the planar mechanism; and
if the cutting plane can be aligned with the target plane, control the actuation unit to bring the cutting plane into alignment with the target plane.

2. The surgical system of claim 1, wherein the cutting tool is a surgical saw comprising a saw blade configured to oscillate within a determined cutting plane.

3. The surgical system of claim 1, wherein the planar mechanism comprises at least two motorized degrees of freedom.

4. The surgical system of claim 1, further comprising a locking system adapted for locking the planar mechanism once the cutting plane has been aligned with the target plane.

5. The surgical system of claim 1, wherein the planar mechanism is passive.

6. The surgical system of claim 1, wherein the actuation unit has three rotational degrees of freedom.

7. The surgical system of claim 6, wherein at least two of the rotational degrees of freedom have respective rotational axes that are substantially orthogonal to each other.

8. The surgical system of claim 1, wherein the control unit is configured to allow actuation of the cutting tool only when the cutting plane is aligned with the target plane.

9. The surgical system of claim 1, wherein the control unit is configured to activate the actuation unit to displace a plane defined by the planar mechanism in a direction orthogonal to said plane as long as the cutting plane is aligned with the target plane.

10. The surgical system of claim 1, wherein the cutting tool rests on the planar mechanism via an interface.

11. A surgical system, comprising:
a surgical saw comprising a saw blade configured to oscillate within a determined cutting plane, the saw having an attached tracker;
a planar mechanism having a first end connected to the saw;
an actuation unit connected to a second end of the planar mechanism, the actuation unit for adjusting a position and orientation of the saw, wherein the actuation unit has a serial architecture and at least three motorized degrees of freedom;
a passive articulated lockable holding arm connected to the actuation unit; and
a control unit configured to:
determine a pose of the saw using data from sensing of the tracker;
determine a cutting plane based on the pose of the cutting tool, wherein the cutting plane is orthogonal to a plane defined by the planar mechanism;
detect whether the cutting plane can be aligned with a target plane for an anatomical structure of a patient; and
if the cutting plane can be aligned with the target plane, control the actuation unit to constrain the planar mechanism to a plane orthogonal to the target plane, thereby aligning the cutting plane with the target plane.

12. The surgical system of claim 11, wherein the saw blade has a target line defined by a position and orientation.

13. The surgical system of claim 12, wherein the planar mechanism constrains the saw blade to the target line.

14. The surgical system of claim 12, wherein the actuation unit displaces the saw by changing the planar mechanism plane while a cutting action of the saw is enabled.

15. The surgical system of claim 14, wherein the control unit is further configured to stop the actuation unit from changing the planar mechanism plane if the planar mechanism orientation or position deviates from the target line more than a predetermined threshold.

16. The surgical system of claim 14, wherein the control unit is further configured to stop the actuation unit from changing the planar mechanism plane if a limit of the saw blade along the target line is reached.

17. The surgical system of claim 14, wherein the control unit is further configured to switch the cutting action on or off.

18. The surgical system of claim 14, wherein the control unit is further configured to change a speed with which the actuation unit changes the planar mechanism plane based on the saw blade's level of advancement along the target line.

19. A surgical system, comprising:
   a surgical saw comprising a saw blade configured to oscillate within a determined cutting plane, the saw having an attached tracker;
   a planar mechanism having a first end connected to the saw;
   an actuation unit connected to a second end of the planar mechanism, the actuation unit for adjusting a position and orientation of the saw, wherein the actuation unit has a serial architecture and at least three motorized degrees of freedom; and
   a control unit configured to:
      determine a pose of the saw using data from sensing of the tracker;
      determine a cutting plane based on the pose of the cutting tool, wherein the cutting plane is orthogonal to a plane defined by the planar mechanism, and wherein the saw blade has a target line defined by a position and orientation;
      detect whether the cutting plane can be aligned with a target plane for an anatomical structure of a patient; and
      if the cutting plane can be aligned with the target plane, control the actuation unit to constrain the planar mechanism to a plane orthogonal to the target plane, thereby aligning the cutting plane with the target plane, wherein the planar mechanism constrains the saw blade to the target line.

20. The surgical system of claim 19, wherein the control unit is further configured to:
   switch the cutting action on or off; or
   stop the saw blade from advancing if a limit of the saw blade along the target line is reached.

* * * * *